(12) United States Patent
Seshadri et al.

(10) Patent No.: US 9,914,931 B2
(45) Date of Patent: Mar. 13, 2018

(54) NANNOCHLOROPSIS SPLICED LEADER SEQUENCES AND USES THEREFOR

(71) Applicant: Synthetic Genomics, Inc., La Jolla, CA (US)

(72) Inventors: Rekha Seshadri, San Diego, CA (US); Ariel S. Schwartz, San Diego, CA (US); Leah Soriaga, San Diego, CA (US); Robert C. Brown, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 14/098,270

(22) Filed: Dec. 5, 2013

(65) Prior Publication Data

US 2014/0186842 A1 Jul. 3, 2014

Related U.S. Application Data

(60) Provisional application No. 61/734,499, filed on Dec. 7, 2012.

(51) Int. Cl.
  *C12N 15/79* (2006.01)
  *C12Q 1/68* (2006.01)
  *C12N 15/67* (2006.01)

(52) U.S. Cl.
  CPC ........... *C12N 15/79* (2013.01); *C12Q 1/6876* (2013.01); *C12N 15/67* (2013.01)

(58) Field of Classification Search
  None
  See application file for complete search history.

(56) References Cited

U.S. PATENT DOCUMENTS

| | | | | |
|---|---|---|---|---|
| 5,512,439 | A * | 4/1996 | Hornes | C12N 15/102 435/6.11 |
| 6,337,391 | B1 * | 1/2002 | Harris | C07K 16/18 435/252.3 |
| 2005/0186597 | A1 | 8/2005 | Michels et al. | |
| 2006/0174365 | A1 | 8/2006 | Werner et al. | |
| 2010/0192258 | A1 | 7/2010 | Benning et al. | |
| 2011/0059495 | A1 | 3/2011 | Bailey et al. | |
| 2011/0158946 | A1 | 6/2011 | Durvasula et al. | |
| 2011/0177575 | A1 * | 7/2011 | Singh | C12N 1/20 435/167 |
| 2012/0220021 | A1 | 8/2012 | Shin et al. | |
| 2013/0131330 | A1 | 5/2013 | Kilian et al. | |
| 2013/0323780 | A1 | 12/2013 | Schneider et al. | |

FOREIGN PATENT DOCUMENTS

| | | | | |
|---|---|---|---|---|
| WO | WO 0157209 | A2 * | 8/2001 | C07K 14/47 |
| WO | WO 2008143679 | A2 * | 11/2008 | C12Y 302/01004 |

OTHER PUBLICATIONS

GenBank Accession No. U71602: *Nannochloropsis* sp. violaxanthin/chlorophyll a binding protein precursor (NANVCP) mRNA, complete cds (Jan. 3, 1998 [online]. [Retrieved on Sep. 26, 2015], Retrieved from the Internet <URL: http://www.ncbi.nlm.nih.gov/nuccore/u71602>.*
Nolan et al. (Nature Protocols (2006) 1: 1559-1582.*
Bustin et al. Clinical Chemistry (2009) 55: 611-622.*
Machine translation of WO 2001/157209 A2; 7 pages.*
GenBank Accession No. JU980781: TSA: Nannochloropsis gaditana CCMP526 NGA_Contig25328 mRNA sequence (May 16, 2012 [online]. [Retrieved on Jul. 12, 2017], Retrieved from the Internet <URL: https://www.ncbi.nlm.nih.gov/nuccore/JU980781>.*
JU978150, GenBank Accession No. JU978150, TSA: Nannochloropsis gaditana CCMP526 NGA Contig36661 mRNA sequence, May 16, 2012 [online]. [Retrieved on Feb. 5, 2014]. Retrieved from the Internet <URL: http://www.ncbi.nlm.nih.gov/nuccore/JU978150> entire document.
Radakovits et al.: "*Draft genome sequence and genetic transformation of the oleaginous alga Nannochioropis gaditana.*"; Nat Commun, Feb. 21, 2012, vol. 3, pp. 686.
Zhang et al.: "*Spliced leader RNA trans-splicing in dinoflagellates*" Proc Natl Acad Sci U S A.; Mar. 13, 2007, vol. 104, No. 11, pp. 4618-4623.
Glanz et al.: "*Trans-splicing of organelle introns—a detour to continuous RNAs*" Bioessays, Sep. 2009, vol. 31, No. 9, pp. 921-934.
Kuo et al.: "*Transcriptomic study reveals widespread spliced leader trans-splicing, short 5'-UTRs and potential complex carbon fixation mechanisms in the euglenoid Alga Eutreptiella sp PLoS One*"; Apr. 9, 2013, vol. 8, No. 4, p. e60826; (12 pages).
International Search Report Re PCT/US2013/073402, dated Mar. 4, 2014.
Clontech Laboratories, Inc., SMARTer™ PCR cDNA Synthesis Kit User Manual, (Jan. 2012).
Ganot et al.,"Spliced-Leader RNA *trans* Splicing in a Chordate, *Oikopleura dioica*, with a Compact Genome", Mol. and Cell. Biology, vol. 24, No. 17, pp. 7795-7805, Sep. 2004.
Hastings, "SL trans-splicing: easy come or easy go?", TRENDS in Genetics, vol. 21, No. 4, pp. 240-247, Apr. 2005.
Lall et al., "Contribution of Trans-splicing, 5' Leader Length, Cap-Poly(A) Synergism, and Initiation Factors to Nematode Translation in an *Ascaris suum* Embryo Cell-free System", J. Biol. Chem., vol. 279, No. 44, pp. 45573-45585, Oct. 2004.
Papers of the Week: "Trans-splicing Promotes Translation", J. Biol. Chem. 2004, 279:e99920.
Lin et al., "Spliced leader-based metatranscriptomic analyses lead to recognition of hidden genomic features in dinoflagellates", PNAS, vol. 107, No. 46, pp. 20033-20038, Nov. 2010.

(Continued)

*Primary Examiner* — Angela M Bertagna
(74) *Attorney, Agent, or Firm* — DLA Piper LLP (US)

(57) ABSTRACT

The present invention relates to the culture and manipulation of microorganisms for biotech applications, and is based on the discovery and characterization of spliced leader sequences identified in transcripts from *Nannochloropsis* species. In particular, the invention provides nucleic acid compositions comprising a SL sequence operably linked to a protein-encoding gene. Further provided are compositions and methods for enhanced gene expression in recombinant microorganisms as well as methods for identification and/or isolation of nucleic acid molecules tagged with a spliced leader sequence.

17 Claims, 5 Drawing Sheets

(56) References Cited

OTHER PUBLICATIONS

Mayer et al., "Pre-mRNA trans-splicing: from kinetoplastids to mammals, an easy language for life diversity", Mem Inst Oswaldo Cruz, Rio de Janeiro, vol. 100(5):501-513, Aug. 2005.
Radakovits et al., "Draft genome sequence and genetic transformation of the oleaginous alga Nannochloropsis gaditana", Nature Communications vol. 3. No. 686, pp. 1-10, Feb. 2012.
Roche Diagnostics GmbH, PCR Applications Manual 3rd Edition, 2006.
Roux, Kenneth "Optimization and Troubleshooting in PCR", Cold Spring Harbor Protocols, Nov. 2013.
Lin et al., Spliced leader-based meta-transcriptomic analyses lead to recognition of hidden genomic features in dinoflagellates, PNAS, vol. 107, No. 46, 20033-20038, Nov. 2010.
Lin et al., "Supporting Information", 10.1073/PNAS.1007246107.
Zohar et al, "Labeling DNA for Single-Molecule Experiments: Methods of Labeling Internal Specific Sequences on Double-Stranded DNA", Nanoscale, vol. 3. No. 8, pp. 3027-3039, Aug. 2011.
Zhang et al., "Retrieval of Missing Spliced Leader in Dinoflagellates", PloS One., vol. 4, No. 1, e4129, Jan. 2009.

\* cited by examiner

ALIGNMENTS
>NODE_32537_length_1897_cov_24.227728:1..1925 (*N. salina* CCMP1776)
Length=1925
Score = 95.5 bits (216), Expect = 1E-19
Identities = 54/54 (100), Gaps = 0/54 (0)
Strand = Plus/Plus Query (SEQ ID NO:7) 1    CAGTAAAGTATTCAAGAATAAACAAAACAATCCCTAAGGGAAAACAACAG    54
                         ||||||||||||||||||||||||||||||||||||||||||||||||||
Sbjct (SEQ ID NO:8) 907  CAGTAAAGTATTCAAGAATAAACAAAACAATCCCTAAGGGAAAACAACAG    960

FIG. 3

```
Ng_3730_4:536775  (SEQ ID NO:13)   TCACACTCTGGTTGTGTGGCCCATCGTGTATATAGGGAGCAGTGTTTCCTCTCTTCTCCCAA
Ng_3730_7:230045  (SEQ ID NO:9)    TCACACCCTGGTTGTGTGGCCCATGGTATAGAGGGAGGAGGAGTGTTTCTCCACCTCGCTCAA
Ng_3730_24:546744 (SEQ ID NO:11)   TCACACTCTGGTTGTGTGGCCCATCGGGTCCGTCGGGAGGAGTGTTTCTCCGTCCATCTCAA
Ng_3730_9:189744  (SEQ ID NO:10)   TCACACTCTGGTTGTGTGGCCCATGGGGTACGTAGGGAGGAGTGTTTCTCCGCCTCTCCCAA
Ng_3730_27:43     (SEQ ID NO:12)   ------------------------------------------------------------CAA
                                                                                              ***

Ng_3730_4:536775  (SEQ ID NO:13)   TTTTTCAGTAAAGTATTCAAGAATAAACAAAACAAAACAATCCTTAAGGGAAAACAACAGGT
Ng_3730_7:230045  (SEQ ID NO:9)    TTTTCAGTAAAGTATTCAAGAATAAACAAACAATCAAACAATCCCTAAGGGAAAACAACAGGT
Ng_3730_24:546744 (SEQ ID NO:11)   TTTTCAGTAAAGTATTCAAGAATAAACAAACAATAAACAAACAATCCCTAAGGGAAAACAACAGGT
Ng_3730_9:189744  (SEQ ID NO:10)   TTTTCAGTAAAGTATTCAAGAATAAACAAACAATAAACAAAACAATCCCTAAGGGAAAACAACAGGT
Ng_3730_27:43     (SEQ ID NO:12)   TTTTCAGTAAAGTATTCAAGAATAAACAAACAAAACAATCCCTAAGGGAAAACAACAGGT
                                    *********************           ****  ***********************

Ng_3730_4:536775  (SEQ ID NO:13)   AATTTGAGCTTTCCAAGCACACTACCCTCCAGACACCTACAACGAACCCCACCTAGATCC
Ng_3730_7:230045  (SEQ ID NO:9)    AATTTGAGCTTCCAAGCACACATCACCCTCCAGACACATCACCCTCCAGATCAATGCGCTTGAAACCCTCCTAGATCC
Ng_3730_24:546744 (SEQ ID NO:11)   AATTTGAGCTTCCAAGCGCATCACATCACCCTCCAGACATCCGGATAACCACGATGAACACTAGATCC
Ng_3730_9:189744  (SEQ ID NO:10)   AATTTGAGCTTCCAAGCACACATCACCCTCACCCTCCGGATAACCACGATGAACACTGATCC
Ng_3730_27:43     (SEQ ID NO:12)   AATTTGAGCTTCCAAGCGCACACATCACCCTCCAGACACCACTACTGAACCCCACCTAGATCC
                                    ***********   ***     *    ********   *    *** *** ** ********

Ng_3730_4:536775  (SEQ ID NO:13)   CTAAACTACCTCACCTGTCTTCTTCCTTCACATCCACAC
Ng_3730_7:230045  (SEQ ID NO:9)    CTAACCAACCTTACCACACCATGCCGTAGTCACATGC
Ng_3730_24:546744 (SEQ ID NO:11)   CTAACTACCTTCCCACACGCCCCTCCTGCTCATGCGT
Ng_3730_9:189744  (SEQ ID NO:10)   CTAAACAATGATTCTTGATGGAAGGTATCGGCGGTTC
Ng_3730_27:43     (SEQ ID NO:12)   CTAAACAACCTCAACACGTACACGTCTGCCCATACCCT
                                   **** * *                                           *
```

FIG. 4

NANNOCHLOROPSIS SPLICED LEADER SEQUENCES AND USES THEREFOR

CROSS-REFERENCE TO RELATED APPLICATIONS

This application claims priority under 35 U.S.C. § 119(e) to U.S. Provisional Patent Application No. 61/734,499, filed on Dec. 7, 2012, the entire contents of which is herein incorporated by reference.

INCORPORATION OF SEQUENCE LISTING

This application contains references to nucleic acid sequences which have been submitted concurrently herewith as the sequence listing text file "SGI-059.20US_Sequence Listing", created on Oct. 1, 2013. The file is 6 kilobytes (kb), and can be assessed using Microsoft Word on a computer that uses Window OS. The aforementioned sequence listing is hereby incorporated by reference in its entirety pursuant to 37 C.F.R. § 1.52(e)(iii)(5).

FIELD OF THE INVENTION

The present disclosure relates generally to the field of molecular biology and the genetic engineering of microorganisms for biotech applications. In particular, the disclosure relates to the discovery and characterization of spliced leader (SL) sequences in transcripts from heterokont species and there use in recombinant expression systems in microorganisms such as, for example, microalgae and heterokont microorganisms. Methods for identification and/or selective cloning of mRNA using a *Nannochloropsis* SL sequence are also disclosed.

BACKGROUND OF THE INVENTION

Spliceosomal trans-splicing generally involves the intermolecular ligation of RNA sequences derived from two independent RNA molecules. A form of trans-splicing is spliced leader (SL) trans-splicing in which a short RNA leader sequence, the spliced leader (approximately 15-50 nt), is transferred from the 5' end of a specialized non-messenger RNA molecule (SL donor RNA) onto unpaired splice-acceptor sites on pre-mRNA molecules to become the 5'-end of the mature mRNA. As a result, diverse mRNAs acquire a common 5' leader sequence.

SL RNAs, the RNAs that contribute or "donate" the spliced leader to another RNA transcript, are short RNAs (approximately 45-140 nt) that contain a splice-donor site but no splice-acceptor site. Although SL RNAs have little primary sequence conservation across phyla, various SL RNA sequences share a conserved, three-stem-loop secondary structure (see, for review, Mayer and Floeter-Winter, *Mem. Inst. Oswaldo Cruz* 100:501-13, 2005). They have an overall structural similarity to Sm-class U-rich small nuclear RNAs (snRNAs) which are present in spliceosomal small ribonucleoprotein complexes (snRPNs) and participate in the splicing mechanism. The splice-donor site functionally divides the SL RNA molecule into two segments. During splicing, the 5'-segment (i.e. the leader sequence) behaves like the first exon in a conventionally-expressed gene, and the 3'-segment behaves like the 5'-part of a conventional intron that gets "spliced out" when the splicing product is generated. SL RNAs are associated with spliceosomal (Sm) proteins and specific non-Sm proteins that interact in vivo with other splicing components in snRPNs.

SL trans-splicing has been considered as a general mechanism that may be required for the production of mature transcripts in some species. It has been further documented that in some cases spliced leaders also play a role in enhancing gene expression. Their proposed functions in this regard include (i) increasing the stability of trans-spliced transcripts, (ii) enabling or enhancing the transport of mature transcripts out of the nucleus to the cytoplasm where they are subsequently translated, and (iii) facilitating the assembly of complete ribosome with large and small subunits at the AUG initiation codon, thereby allowing efficient translation. Other roles for SLs in various species include: providing a 5'-cap structure for protein-coding RNAs transcribed by the rRNA polymerase, Pol I; generating mature monocistronic mRNAs from polycistronic pre-mRNA transcripts; and other roles, as reviewed previously (Hastings et al., *Trends in Genetics* 21:240-47, 2005). In some instances, SL trans-splicing can turn polycistronic transcripts into translatable, monocistronic mRNAs by transplanting a short (about 15-50 nucleotide) fragment from a donor RNA—the SL sequence—onto the 5' ends of separate pre-mRNAs transcribed as one, long polycistron. Each pre-mRNA in the polycistron has an intron that contains a spliceosomal (Sm) binding site believed to facilitate splicing.

SL trans-splicing has been studied extensively in Euglenozoa and has been detected in a limited but diverse number of eukaryotes including appendicularia, ascidians, cnidarians, nematodes, Platyhelminthes, and rotifers. More recently, SL RNA trans-splicing with a unique and conserved spliced leader sequence (22-nt) has been reported in a number of dinoflagellates (Zhang et al. *Proc. Natl. Acad. Sci. USA* 104:4618-4623, 2007).

SUMMARY OF THE INVENTION

The present disclosure generally relates to the discovery and characterization of spliced leader (SL) sequences identified in transcripts from microalgal species of *Nannochloropsis*, which constitutes the first report of SL trans-splicing in a genus within the chromists (which includes stramenopiles or heterokonts, along with haptophytes and cryptomonads).

The disclosure also relates to compositions and methods for enhanced gene expression. Obtaining high expression of recombinant proteins has been one of the major challenges within the biotechnology industry. 5' non-translated regions of an mRNA can play an important role in translation and therefore in the regulation of gene expression. The invention provides a composition comprising an 18-nt non-translated leader sequence operably linked to a coding sequence such as, for example a gene sequence that encodes a desired polypeptide.

The present disclosure further relates to methods for identification and/or selective isolation of mRNAs that are tagged with a 5' SL sequence from a heterokont species, such as a *Nannochloropsis* sp. Gene discovery through conventional cDNA libraries has certain limitations, such as the difficulty in obtaining complete cDNAs and contamination with rRNA, mitochondrial or chloroplast RNA transcripts, and genomic DNA. In the case of mixtures of cells of different species, it may also be difficult to avoid contamination with heterologous cDNA or genomic clones. The presently disclosed method for identification and/or selective isolation of cDNAs provides a solution for the need in identifying species-specific full-length cDNAs or in construction of cDNA libraries enriched in full-length cDNA molecules.

In one aspect, the present invention provides isolated or recombinant nucleic acid molecules comprising nucleic acid sequences, referred to herein as SL or SL-homologous sequences, that have at least 80%, at least 83%, at least 85%, for example at least 88%, about 89%, at least 90%, at least 93%, at least 94%, at least 95%, or 100% sequence identity to a nucleic acid sequence selected from the group consisting of SEQ ID NO:1; SEQ ID NO:2; SEQ ID NO:3; SEQ ID NO:4; SEQ ID NO:5; SEQ ID NO:6; and a complement of any thereof; in which the nucleic acid sequence is operably linked to a heterologous nucleic acid sequence. In some examples an isolated or recombinant nucleic acid molecule of the invention comprises a nucleic acid sequence that has at least 80%, at least 83%, at least 85%, for example at least 88%, about 89%, at least 90%, at least 93%, at least 94%, at least 95%, or 100% sequence identity to a nucleic acid sequence selected from the group consisting of SEQ ID NO:2; SEQ ID NO:3; and SEQ ID NO:4. In some examples an isolated or recombinant nucleic acid molecule of the invention comprises a nucleic acid sequence according to SEQ ID NO:5 or SEQ ID NO:6. In some examples, the heterologous nucleic acid molecule operably linked to the SL or SL-homologous sequence includes a regulatory element, for example, a heterologous promoter. In some examples, the heterologous nucleic acid sequence operably linked to the SL or SL-homologous sequence comprises coding sequence for a polypeptide. The protein encoding-sequence can be a sequence that is not identical to a protein-encoding sequence of the same species the SL sequence it is operably linked to is derived from. In some examples, the SL sequence is from a *Nannochloropsis* species and the protein-encoding sequence is not 100% identical to a protein-encoding sequence of the same *Nannochloropsis* species.

Further provided are nucleic acid constructs such as, e.g., expression cassettes and vectors, which include a nucleic acid molecule of the invention as described herein. In such nucleic acid constructs, the nucleic acid molecule includes a nucleic acid sequence having at least 80%, at least 83%, at least 85%, for example at least 88%, about 89%, at least 90%, at least 93%, at least 94%, at least 95%, or 100% sequence identity to a nucleic acid sequence selected from the group consisting of SEQ ID NO:1, SEQ ID NO:2, SEQ ID NO:3, SEQ ID NO:4, SEQ ID NO:5, SEQ ID NO:6, and a complement of any thereof; in which the nucleic acid sequence is operably linked to a heterologous nucleic acid. For example, a construct can include an SL or SL-homologous sequence as provided herein operably linked to, and positioned downstream of, a promoter. Alternatively or in addition, a construct can include an SL or SL-homologous sequence as provided herein operably linked to, and positioned upstream of, a protein-encoding nucleic acid sequence. The protein encoding-sequence can be a sequence that is not identical to a protein-encoding sequence of the same species the SL sequence it is operably linked to is derived from. The construct can in some examples be in an expression vector. In some examples, the construct can be an expression cassette.

In a further aspect, the present invention provides isolated or recombinant nucleic acid molecules comprising nucleic acid sequences that have at least 80%, at least 83%, at least 85%, for example at least 88%, about 89%, at least 90%, at least 93%, at least 94%, at least 95%, such as 100% sequence identity to a nucleic acid sequence selected from the group consisting of SEQ ID NO:1, SEQ ID NO:2, SEQ ID NO:3, SEQ ID NO:4, SEQ ID NO:5, SEQ ID NO:6, and a complement of any thereof, in which the nucleic acid molecules are less than about 250 nucleotides in length, for example, less than about 200 nucleotides, less than about 180 nucleotides, less than about 150 nucleotides, less than about 100 nucleotides, less than about 80 nucleotides, or less than about 65 nucleotides in length. In some examples an isolated or recombinant nucleic acid molecule of the invention comprises a nucleic acid sequence that has at least 80%, at least 83%, at least 85%, for example at least 88%, about 89%, at least 90%, at least 93%, at least 94%, at least 95%, or 100% sequence identity to a nucleic acid sequence selected from the group consisting of SEQ ID NO:2, SEQ ID NO:3, and SEQ ID NO:4 and has a length of less than about 250, less than about 200, less than about 150, or less than about 100 nucleotides. In some examples an isolated or recombinant nucleic acid molecule of the invention comprises a nucleic acid sequence conforming to SEQ ID NO:5 or SEQ ID NO:6 and has a length of less than about 250, less than about 200, less than about 150, or less than about 100 nucleotides. The isolated or recombinant nucleic acid molecule can comprise one or more additional nucleic acid sequences juxtaposed with the nucleic acid sequence having at least 80% sequence identity to SEQ ID NO:1, SEQ ID NO:2, SEQ ID NO:3, SEQ ID NO:4, SEQ ID NO:5, or SEQ ID NO:6 that are heterologous with respect to SEQ ID NO:1, SEQ ID NO:2, SEQ ID NO:3, SEQ ID NO:4, SEQ ID NO:5, or SEQ ID NO:6, i.e., not found juxtaposed with the SL sequence in nature. The isolated or recombinant nucleic acid molecule can be an oligonucleotide, i.e., a nucleic acid sequence of about 100 nucleotides or less, and can be DNA or RNA.

A nucleic acid molecule as provided herein (e.g., a nucleic acid molecule comprising a sequence having at least 80% identity (e.g., at least 83%, at least 88%, about 89%, at least 93%, or 100% identity) to SEQ ID NO:1, SEQ ID NO:2, SEQ ID NO:3, SEQ ID NO:4, SEQ ID NO:5, or SEQ ID NO:6 operably linked to a heterologous sequence) can comprise or be covalently or noncovalently bound to a detectable label, for example, a fluorescent or isotopic label, or a small molecule, binding moiety, or enzyme that can generate a detectable signal or bind a moiety that produces a detectable signal under appropriate detection conditions. Alternatively or in addition, a nucleic acid molecule as provided herein can be covalently or noncovalently bound to a solid support, such as a filter, chip, array, bead, column, etc.

In another aspect, the present invention provides a host cell that comprises a nucleic acid molecule as disclosed herein, such as a nucleic acid molecule comprising a sequence having at least 80% identity (e.g., at least 83%, at least 88%, about 89%, at least 93%, or 100% identity) to SEQ ID NO:1, SEQ ID NO:2, SEQ ID NO:3, SEQ ID NO:4, SEQ ID NO:5, SEQ ID NO:6 operably linked to a heterologous sequence, such as any disclosed herein. The host cell can be a microbial cell. In some examples, the host cell is an algal cell or a heterokont cell. In some examples, the host cell is a *Nannochloropsis* cell.

In yet another aspect, also provided are methods for enhancing expression of a gene of interest in a host cell. The methods include expressing in the host cell an isolated nucleic acid molecule comprising a nucleic acid sequence having at least 80%, at least 83%, at least 85%, for example at least 88%, about 89%, at least 90%, at least 93%, such as at least 95%, or 100% sequence identity to a nucleic acid sequence selected from the group consisting of SEQ ID NO:1, SEQ ID NO:2, SEQ ID NO:3, SEQ ID NO:4, SEQ ID NO:5, SEQ ID NO:6, in which the nucleic acid sequence is operably linked to a heterologous nucleic acid that comprises a coding sequence for the gene of interest. For example, the nucleic acid molecule expressed in the cell can comprise a nucleic acid sequence having at least 80%, at least 83%, at least 85%, for example at least 88%, about 89%, at least 90%, at least 93%, such as at least 95%, or 100% sequence identity to a nucleic acid sequence selected from the group consisting SEQ ID NO:2, SEQ ID NO:3, and SEQ ID NO:4 operably linked to a heterologous protein-encoding sequence; or alternatively or in addition can comprise a nucleic acid sequence conforming to SEQ ID NO:5 or SEQ ID NO:6 operably linked to a heterologous protein-encoding sequence. The host cell can be, for example, a cell of a *Nannochloropsis* species, and the gene can be derived from a species other than a *Nannochloropsis* species. In various examples, the cell is a heterokont cell or a *Nannochloropsis* cell, e.g., a *N. gaditana, N. salina*, or *N. oceanica* cell.

In a further aspect of the invention, there are provided methods for identifying or isolating a nucleic acid molecule derived from a cell, optionally in a mixed cell culture. The methods include hybridizing at least one nucleic acid molecule comprising an SL or SL-homologous sequence as disclosed herein (e.g., a nucleic acid sequence having at least 80% sequence identity to SEQ ID NO:1, SEQ ID NO:2, SEQ ID NO:3, SEQ ID NO:4, SEQ ID NO:5, or SEQ ID NO:6 or a complement of any thereof) with a population of nucleic acid molecules, e.g., RNA or cDNA molecules, derived from the cell or a cell culture comprising the cell. In some examples, the nucleic acid molecules used to hybridize to a population cell-derived nucleic acid molecules can comprise a nucleic acid sequence having at least 80%, at least 83%, at least 85%, for example at least 88%, about 89%, at least 90%, at least 93%, at least 94%, such as at least 95%, or 100% sequence identity to a nucleic acid sequence selected from the group consisting of SEQ ID NO:2, SEQ ID NO:3, SEQ ID NO:4, and a complement of any thereof; or alternatively or in addition can comprise a nucleic acid sequence selected from the group consisting of a nucleic acid sequence according to SEQ ID NO:5, a nucleic acid sequence according to SEQ ID NO:6, and a complement of either. In various examples, the methods may include one or more of the following additional steps: performing at least one reverse transcription reaction, e.g., using a 3' primer for first strand cDNA synthesis; performing at least one polymerase reaction, e.g., a reaction using a DNA polymerase using at least one primer comprising an SL or SL-homologous sequence as disclosed herein; and amplifying a nucleic acid sequence of the population of nucleic acid molecules. In some examples, amplifying a nucleic acid sequence can be performed by polymerase chain reaction (PCR) with at least one primer comprising a nucleic acid molecule comprising an SL-homologous sequence as disclosed herein, in which the amplification template includes one or more reverse transcription products (cDNA5) derived from one or more RNA molecules isolated from the cell or cell culture. In some examples, the methods of this aspect may include a step of isolating from a population of nucleic acid molecules one or more nucleic acid molecules that hybridize with the primer. In some examples, the reverse transcription reaction and/or the amplification reactions are performed using at least one 3' primer selected from the group consisting of a gene-specific primer, an oligo-dT primer, a population of random primers, and a degenerate primer. In various examples, the cell is a heterokont cell or a *Nannochloropsis* cell, e.g., a *N. gaditana, N. granulata, N. limnetica, N. maritime, N. aceanica, N. oculata*, or *N. salina* cell.

Also provided herein are methods of generating a cDNA or a cDNA library using a 3' primer for reverse transcriptase such as, for example, a primer comprising oligodT, a degenerate primer, a population of random primers, or a gene-specific or gene family-specific primer and a 5' primer for second strand synthesis, in which the second primer is a nucleic acid molecule as disclosed herein that comprises an SL sequence or SL-homologous sequence. For example, the nucleic acid molecule used as a primer for cDNA synthesis can have at least 80%, at least 83%, at least 85%, for example at least 88%, about 89%, at least 90%, such as at least 93%, at least 94%, at least 95%, or 100% sequence identity to a nucleic acid sequence selected from the group consisting SEQ ID NO:2, SEQ ID NO:3, and SEQ ID NO:4; or alternatively or in addition can comprise a nucleic acid sequence conforming to SEQ ID NO:5 or SEQ ID NO:6. In some examples, the cell or cell population from which the RNA is isolated is or comprises a heterokont cell and in some examples cell or cell population from which the RNA is isolated comprises a *Nannochloropsis* cell, e.g., a *N. gaditana, N. granulata, N. limnetica, N. maritime, N. aceanica, N. oculata*, or *N. salina* cell.

Also provided herein are kits for identifying or isolating a nucleic acid molecule from a cell or cell culture, and/or for synthesizing a cDNA or cDNA library. The kits include at least an oligonucleotide comprising a nucleic acid molecule as disclosed herein and at least one of a polymerase, a polymerase buffer, a hybridization or binding buffer, a detectable label, one or more reagents for isolation of RNA, a solid support, an additional oligonucleotide such as a polyT-containing oligonucleotide a preparation of mixed oligonucleotides, and a cloning vector.

These and other objects and features of the invention will become more fully apparent from the following detailed description of the invention, Examples, and the claims.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2B is a graphical representation of a *Nannochloropsis* SL consensus motif (SEQ ID NO:6).

FIG. 3 is a sequence alignment of the *Nannochloropsis gaditana* SL donor template sequence (Query; SEQ. ID NO:7) to the *N. salina* CCMP1776 genome (Sbjct; SEQ ID NO:8). Nucleotide residues corresponding to the spliced leader (SL) are identified by boxed segments of the aligned sequences.

FIG. 4 is a sequence alignment of the putative donor sequences from the 5 distinct genetic loci identified in *Nannochloropsis gaditana* and described in Example 1. Identical nucleotide residues corresponding to the spliced leader (SL) followed by a splice donor site GT are identified by boxed segments of the aligned sequences.

FIG. 5 depicts the results of an agarose gel electrophoresis analysis of SL-based full-length cDNA products from *Nan-* nochloropsis sp. Agarose gel photos illustrate the quality of cDNA produced by PCR-amplification using three primer combinations. 1) "Oligo dT" lanes: an oligo dT primer paired with a commercial generic 5' primer (Clontech 5' SMART primer); 2) "Random" lanes: a random 3' primer primed with a commercial generic 5' primer (Clontech 5' SMART primer); and 3) "SL+oligo dT" lanes: an Oligo dT 3' primer paired with a 5' primer corresponding to a spliced leader sequence. Lanes M: 1-kb DNA ladder.

DETAILED DESCRIPTION OF THE INVENTION

Figure 1:
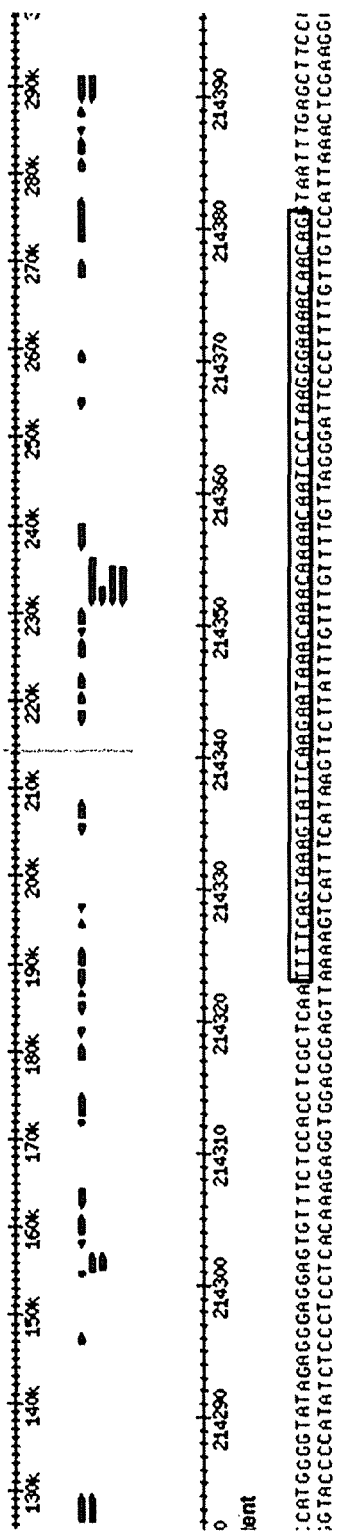
FIG. 1 demonstrates a putative donor site (SEQ ID NO:7) identified in a nuclear assembly to which the SL RNA sequence was mapped.

The present invention is based on the discovery and characterization of spliced leader (SL) sequences identified in transcripts from *Nannochloropsis* species. SL sequence trans-splicing has never been reported in *Nannochloropsis* or in any closely related genera, including any genus of the stramenopile lineage. The term "heterokont," as used herein, refers to an organism of the "stramenopile" lineage, and the terms "heterokont" and "stramenopile" are to be understood as interchangeable in their use throughout the present disclosure.

In particular, the invention provides nucleic acid compositions comprising a trans-spliced leader sequence operably linked to a heterologous nucleic acid such as, for example a structural gene that encodes a protein of interest or a regulatory sequence. The invention further provides compositions and methods useful for enhancing gene expression in recombinant microorganisms such as microalgae and heterokonts. Also provided are methods for identification and/or selective isolation of nucleic acid molecules tagged with an SL sequence of the invention.

Throughout this disclosure, various information sources are referred to and/or incorporated by reference. The information sources include, for example, scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. It should also be noted that the reference to such information sources is solely for the purpose of providing an indication of the general state of the art at the time of filing. While the contents and teachings of each and every one of the information sources can be relied on and used by one of skill in the art to make and use embodiments of the invention, any discussion and comment in a specific information source should in no way be considered as an admission that such comment was widely accepted as the general opinion in the field.

Some Definitions

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, including mixtures thereof "A and/or B" is used herein to include all of the following alternatives: "A", "B", and "A and B".

"About" means within plus or minus 10% of the provided value, inclusive of the provided value. Where ranges are provided, they are inclusive of the boundary values.

As used herein, "amino acid" refers to naturally-occurring and synthetic amino acids, as well as amino acid analogs and amino acid mimetics that function in a manner similar to the naturally-occurring amino acids. Naturally-occurring amino acids are those encoded by the genetic code, including D/L optical isomers, as well as those amino acids that are later modified, e.g., hydroxyproline, y-carboxyglutamate, and O-phosphoserine. Amino acid analogs refer to compounds that have the same basic chemical structure as a naturally-occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics, as used herein, refer to chemical compounds that have a structure that is different from the general chemical structure of an amino acid, but that functions in a manner similar to a naturally-occurring amino acid.

A "cDNA" is a DNA molecule that comprises at least a portion the nucleotide sequence of an mRNA molecule, with the exception that the DNA molecule substitutes the nucleobase thymine, or T, in place of uridine, or U, occurring in the mRNA sequence. A cDNA can be single-stranded or double-stranded, and can be the complement of the mRNA sequence. In preferred embodiments, a cDNA does not include one or more intron sequences that occur in the naturally-occurring gene (in the genome of an organism) that the cDNA corresponds to. For example, a cDNA can have sequences from upstream (5') of an intron of a naturally-occurring gene juxtaposed to sequences downstream (3') of the intron of the naturally-occurring gene, where the upstream and downstream sequences are not juxtaposed in a DNA molecule (i.e., the naturally occurring gene) in nature. A cDNA can be produced by reverse transcription of mRNA molecules by a polymerase (e.g., a reverse transcriptase), or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences or compiled from the sequences of multiple partial cDNAs.

A "coding sequence" or "coding region", as used herein in reference to an mRNA or DNA molecule, refers to the portion of the mRNA or DNA molecule that codes for a polypeptide. It typically consists of the nucleotide residues of the molecule which are matched with an anticodon region of a transfer RNA molecule during translation of the mRNA molecule or which encode a stop codon. The coding sequence may thus include nucleotide residues corresponding to amino acid residues which are not present in the mature protein encoded by the mRNA molecule (e.g., amino acid residues in a protein export signal sequence).

A "control organism", "control microorganism", or "control cell" as used in the present disclosure provides a reference point for measuring changes in phenotype of the subject organism, microorganism, or cell. A control organism, microorganism, or cell may comprise, for example, (a) a wild-type organism, microorganism, or cell, i.e., of the same genotype as the starting material for the genetic alteration which resulted in the subject organism, microorganism, or cell; (b) an organism, microorganism, or cell of the same genotype as the starting material but which has been transformed with a null construct (i.e. a construct which has no known effect on the trait of interest, such as a construct comprising a reporter gene); (c) an organism, microorganism, or cell which is a non-transformed segregant among progeny of a subject organism, microorganism, or cell; or (d) the subject organism, microorganism, or cell itself, under conditions in which the gene of interest is not expressed. In some instances, "control organism" may refer to an organism that does not contain the exogenous nucleic acid present in the transgenic organism of interest, but otherwise has the same or similar genetic background as such a transgenic organism.

"Down-regulation" refers to regulation that decreases production of expression products (mRNA, polypeptide, biological activity, or combinations of any thereof) relative to basal or native states.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "endogenous," within the context of the present disclosure refers to any polynucleotide, polypeptide or protein sequence which is a natural part of a cell or organism.

"Exogenous" with respect to a nucleic acid or gene indicates that the nucleic acid or gene is part of a recombinant nucleic acid construct and is not in its natural environment. For example, an exogenous nucleic acid or gene is from one species and has been introduced ("transformed") into another organism, microorganism, or cell by human intervention. Typically, such an exogenous nucleic acid or gene into a cell or organism via a recombinant nucleic acid construct. An exogenous nucleic acid can be a sequence from one species introduced into another species, i.e., a heterologous nucleic acid. An exogenous nucleic acid can also be a sequence that is native or endogenous to an organism (i.e., the nucleic acid sequence occurs naturally in that species or encodes a polypeptide that occurs naturally in the host species) and that has been reintroduced into cells of that organism. An exogenous nucleic acid that includes an endogenous sequence can often be distinguished from the naturally-occurring sequence by the presence of non-natural sequences linked to the exogenous nucleic acid, e.g., non-native regulatory sequences flanking an endogenous gene sequence in a recombinant nucleic acid construct. Alternatively or in addition, a stably transformed exogenous nucleic acid can be detected or distinguished from a native gene by its juxtaposition to sequences in the genome where it has integrated. A nucleic acid is considered exogenous if it has been introduced into a progenitor of the cell, organism, or strain under consideration.

As used herein, "expression" refers to the process of converting genetic information of a polynucleotide into RNA through transcription, which is typically catalyzed by an enzyme, RNA polymerase, and into protein, through translation of mRNA on ribosomes.

"Expression cassette" as used herein means a DNA sequence capable of directing expression of a particular nucleotide sequence in an appropriate host cell, comprising a promoter operably linked to a nucleotide sequence of interest, which is—optionally—operably linked to termination signals and/or other regulatory elements. An expression cassette may also comprise sequences required for proper translation of the nucleotide sequence. The coding region usually codes for a protein of interest but may also code for a functional RNA of interest, for example antisense RNA or a non-translated RNA, in the sense or antisense direction. The expression cassette comprising the nucleotide sequence of interest may be chimeric, meaning that at least one of its components is heterologous with respect to at least one of its other components. The expression cassette may also be one, which is naturally occurring but has been obtained in a recombinant form useful for heterologous expression. An expression cassette may be assembled entirely extra-cellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. The expression of the nucleotide sequence in the expression cassette may be under the control of a constitutive promoter or of an inducible promoter which initiates transcription only when the host cell is exposed to some particular external stimulus.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Examples of expression vectors known in the art include cosmids, plasmids (e.g., naked or contained in liposomes) and viruses (e.g., retroviruses, lentiviruses, adenoviruses, and adeno-associated viruses) that incorporate the recombinant polynucleotide.

"Fragment", as applied to a nucleic acid, refers to a clone or any part of a polynucleotide molecule that retains a usable, functional characteristic. Useful fragments include oligonucleotides and polynucleotides that may be used in hybridization or amplification technologies or in the regulation of replication, transcription or translation. In the context of the present disclosure, a fragment may ordinarily be any subsequence of a nucleic acid, typically of at least about 9 consecutive nucleotides, at least about 12 consecutive nucleotides, at least about 14 consecutive nucleotides, at least about 16 consecutive nucleotides, more typically from about 10 to 18 consecutive nucleotides, typically from at least about 12 to 16 consecutives nucleotides, even more typically from at least about 10 to 16 consecutive nucleotides, of any one of the nucleotide sequences provided herein in the Sequence Listing.

An "oligonucleotide", as used herein, is a nucleic acid molecule 200 or fewer nucleotides in length. An oligonucleotide can be RNA, DNA, or a combination of DNA and RNA, a nucleic acid derivative, or a synthetic nucleic acid, for example, an oligonucleotide can be a peptide nucleic acid or a locked nucleic acid, and can be single-stranded, double-stranded, or partially single-stranded and partially double-stranded. An oligonucleotide can be, for example, between about 4 and about 200 nucleotides in length, between about 6 and about 200 nucleotides in length, between about 10 and about 200 nucleotides in length, between about 15 and about 200 nucleotides in length, between about 17 and about 200 nucleotides in length, between about 20 and about 200 nucleotides in length, or between about 40 and about 200 nucleotides in length. In additional examples, an oligonucleotide can be between about 15 and about 180 nucleotides in length, between about 15 and about 160 nucleotides in length, between about 15 and about 140 nucleotides in length, between about 15 and about 120 nucleotides in length, between about 17 and about 100 nucleotides in length, between about 17 and about 80 nucleotides in length, or between about 17 and about 70 nucleotides in length, for example between about 20 and about 65 nucleotides in length.

When used in reference to a polynucleotide, a gene, a nucleic acid, a polypeptide, or an enzyme, the term "heterologous" refers to a polynucleotide, gene, a nucleic acid, polypeptide, or an enzyme not derived from the host species, e.g., is from a different species with respect to the host cell. For example, a transgenic *Nannochloropsis* microorganism transformed with the coding sequence for a fatty acid desaturase from a *Tetraselmis* microorganism or from a plant is transformed with a heterologous desaturase gene. When referring to nucleic acid sequences operably linked or otherwise joined to one another in a nucleic acid construct or molecule, "heterologous sequences", as used herein, are those that are not operably linked or are not contiguous to each other in nature. As such, elements operably linked in nature and contiguous to each other are not heterologous to each other. On the other hand, these same elements remain operably linked but become heterologous if other filler sequence is placed between them or if they are operably linked in a novel manner by genetic engineering. For example, a promoter from *Tetraselmis* sp. is considered heterologous to a *Nannochloropsis* coding region sequence. Also, a promoter from a gene encoding a tubulin gene from *Nannochloropsis* is considered heterologous to a sequence encoding a *Nannochloropsis* fatty acid desaturase. Similarly, when referring to a gene regulatory sequence or to an auxiliary nucleic acid sequence used for maintaining or manipulating a gene sequence (e.g. a 5' un-translated region, 3' un-translated region, Kozak sequence, poly A addition sequence, intron sequence, splice site, ribosome binding site, internal ribosome entry sequence, genome homology region, recombination site, etc.), "heterologous" means that the regulatory sequence or auxiliary sequence is from a different source (e.g., different gene, whether from the same or different species as the host organisms) than the gene with which the regulatory or auxiliary nucleic acid sequence is juxtaposed in a construct, genome, chromosome, or episome.

The term "hybridization", as used herein, refers generally to the ability of nucleic acid molecules to join via complementary base strand pairing. Such hybridization may occur when nucleic acid molecules are contacted under appropriate conditions and/or circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, nucleic acid molecules are said to exhibit "complete complementarity" when every nucleotide of one of the molecules is complementary to its base pairing partner nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Nucleic acid molecules that hybridize to other nucleic acid molecules, e.g., at least under low stringency conditions are said to be "hybridizable cognates" of the other nucleic acid molecules. Conventional stringency conditions are described by Sambrook et al., 1989, supra), and by Haymes et al. In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule or fragment thereof of the present invention to serve as a primer or probe it needs only be sufficiently complementary in sequence to be able to form a stable double-stranded structure under the particular solvent and salt concentrations employed.

Appropriate stringency conditions which promote DNA hybridization include, for example, 6.0× sodium chloride/sodium citrate (SSC) at about 45° C., followed by a wash of 2.0×SSC at about 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. These conditions are known to those skilled in the art, or can be found in *Current Protocols in Molecular Biology*, John Wiley & Sons, N.Y. (1989), 6.3.1-6.3.6. For example, low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989, supra). In one embodiment of the present invention, high stringency conditions involve nucleic acid hybridization in about 2×SSC to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. High stringency conditions are typically provided by 6×SSC, 5×Denhardt's solution, 100 mg/mL fish sperm DNA, and 0.1% (w/v) SDS, with incubation at 55×C for several hours. Hybridization is generally followed by several wash steps. The wash compositions generally comprise 0.5×SSC to about 10×SSC, and 0.01% (w/v) to about 0.5% (w/v) SDS with an incubation for 15-min at about 20° C. to about 70° C. Typically, the nucleic acid segments remain hybridized after washing at least one time in 0.1×SSC at 65° C.

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. As such, an "isolated" nucleic acid typically is free of sequences that naturally flank the nucleic acid (i.e., sequences located at the 5' and 3' ends of the nucleic acid) in the cell of the organism from which the nucleic acid is derived. An isolated nucleic acid or protein can be, in some instances, partially or substantially purified, but no particular level of purification is required for isolation. For example, an isolated nucleic acid molecule can be a nucleic acid sequence that has been excised from the chromosome, genome, or episome that it is integrated into in nature. Thus, an isolated nucleic acid includes, without limitation, a nucleic acid that exists as a purified molecule, or a nucleic acid molecule that is incorporated into a vector or a recombinant cell.

A "purified" nucleic acid molecule or nucleotide sequence is substantially free of cellular material and cellular components. The purified nucleic acid molecule may be free of chemicals beyond buffer or solvent, for example. "Substantially free" is not intended to mean that other components beyond the novel nucleic acid molecules are undetectable. In some circumstances "substantially free" may mean that the nucleic acid molecule or nucleotide sequence is free of at least 95% (w/w) of cellular material and components.

The term "mis-expression" refers to an increase or decrease in the transcription of a coding region into a complementary RNA sequence as compared to the parental wild-type, for example, alga or plant. This term also encompasses expression of a gene or coding region for a different time period as compared to the wild-type and/or from a non-natural location within the parental genome. The term "overexpression" or "increased expression" as used herein refers to a greater expression level of a gene, a polynucleotide sequence, or a polypeptide, in a host cell compared to a wild-type cell or a wild-type organism, at any developmental or temporal stage. Methods for increasing expression of genes or gene products are well documented in the art and include, for example, overexpression driven by appropriate promoters (e.g. constitutive promoters), the use of transcription enhancers or translation enhancers. Overexpression may also under control of an inducible or a growth-phase specific promoter. These or other inducible or phase-specific promoters may be incorporated into an expression cassette comprising a transcription factor polynucleotide of the invention, where the promoter is operably linked to the transcription factor polynucleotide, can be envisioned and produced. Thus, overexpression may occur throughout an algal cell for example, in specific growth phases of the algal cell or in the presence or absence of particular environmental signals, depending on the promoter used.

The term "native" is used herein to refer to nucleic acid sequences or amino acid sequences as they naturally occur in the host. The term "non-native" is used herein to refer to nucleic acid sequences or amino acid sequences that do not occur naturally in the host, or are not configured as they are naturally configured in the host. A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome, or genes endogenous to the host organism that are in a locus of the genome other than that where they naturally occur.

In reference to a nucleic acid molecule or a polypeptide, the terms "naturally-occurring" and "wild-type" refer to a form found in nature. For example, a naturally occurring or wild-type nucleic acid molecule, nucleotide sequence or protein may be present in and isolated from a natural source, and is not intentionally modified by human manipulation.

The terms "nucleic acid molecule" and "polynucleotide molecule" are used interchangeably herein, and refer to both DNA and RNA molecule, including cDNA, genomic DNA, synthetic DNA, and DNA or RNA containing nucleic acid analogs. Polynucleotides can have any three-dimensional structure. Polynucleotides can be natural-occurring or synthetic origin. A nucleic acid molecule can be double-stranded or single-stranded (i.e., a sense strand or an anti-sense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

As used herein, "operably linked" is intended to mean a functional linkage between two or more sequences such that activity at or on one sequence affects activity at or on the other sequence(s). For example, an operable linkage between a polynucleotide of interest and a regulatory sequence (e.g., a promoter) is a functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site. Operably linked elements may be contiguous or non-contiguous. When used to refer to the joining of two protein coding regions, by "operably linked" is intended that the coding regions are in the same reading frame. When used to refer to the effect of an enhancer, "operably linked" indicated that the enhancer increases the expression of a particular polypeptide or polynucleotides of interest. "Juxtaposed with" in the context of nucleic acid sequences, means the referenced sequences are part of the same continuous nucleic acid molecule.

The terms "polynucleotide sequence" and "nucleic acid sequence" as used herein interchangeably refer to a sequence of a polynucleotide molecule, and can refer, for example, to DNA or RNA sequences. The nomenclature for nucleotide bases as set forth in 37 CFR §1.822 is used herein.

A "promoter" refers to a transcription control sequence that is capable of initiating transcription in a host cell and can drive or facilitate transcription of a nucleotide sequence or fragment thereof of the instant invention. Such promoters need not be of naturally-occurring sequences. In addition, it will be understood that such promoters need not be derived from the target host cell or host organism.

"Polypeptide" and "protein" are used interchangeably herein and refer to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition. In various embodiments the polypeptides can have at least 10 amino acids or at least 25, or at least 50 or at least 75 or at least 100 or at least 125 or at least 150 or at least 175 or at least 200 amino acids.

As used herein "progeny" means a descendant, offspring, or derivative of an organism. For example, daughter cells from a transgenic alga are progeny of the transgenic alga. Because certain modifications may occur in succeeding generations due to mutations or environmental influences, such progeny, descendant, or derivatives may not, in fact, be identical to the parent cell, but are still included within the scope of the term as used herein.

The terms "recombinant" or "engineered" as used herein in reference to a nucleic acid molecule, refer to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence.

The term "recombinant protein" as used herein refers to a protein produced by genetic engineering, for example, by expression of a genetically engineered nucleic acid molecule in a cell.

The term "regulatory region" "regulatory sequence", "regulatory element", or "regulatory element sequence", as used in the present invention, refer to a nucleotide sequence that influences transcription or translation initiation or rate, and stability and/or mobility of a transcription or translation product. Such regulatory regions need not be of naturally-occurring sequences. Regulatory sequences include but are not limited to promoter sequences, enhancer sequences, response elements, protein recognition sites, inducible elements, protein binding sequences, 5' and 3' un-translated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR).

As used herein, "transgenic organism" refers to an organism which comprises a heterologous polynucleotide. When applied to organisms, the terms "transgenic" or "recombinant" or "engineered" or "genetically engineered," used interchangeably herein, refer to organisms that have been manipulated by introduction into the organism of an exogenous or recombinant nucleic acid sequence. Generally, the heterologous polynucleotide is stably integrated within the genome such that the polynucleotide is passed on to successive generations, although it can also be present on an episome, and may be present on a synthetic chromosome of the transgenic organism. The non-native polynucleotide may be integrated into the genome alone or as part of a recombinant expression cassette. In additional examples, a transgenic microorganism can include an introduced exogenous regulatory sequence operably linked to an endogenous gene of the transgenic microorganism. Non-limiting examples of such manipulations include gene knockouts, targeted mutations and gene replacement, promoter replacement, deletion, or insertion, as well as introduction of transgenes into the organism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases, zinc finger nucleases, talens, or CRISPR nucleases. As used herein, "recombinant microorganism" or "recombinant host cell" includes progeny or derivatives of the recombinant microorganisms of the invention. Because certain modifications may occur in succeeding generations from either mutation or environmental influences, such progeny or derivatives may not, in fact, be identical to the parent cell, but are still included within the scope of the term as used herein.

For nucleic acids and polypeptides, the term "variant" is used herein to denote a polypeptide, protein, or polynucleotide molecule with some differences, generated synthetically or naturally, in their base or amino acid sequences as compared to a reference polypeptide or polynucleotide, respectively, such that the variant has at least 70% sequence identity with the reference polypeptide or polynucleotide. In other embodiments the variant can have at least 80% or at least 90% or at least 95% or at least 97% or at least 98% or at least 99% sequence identity with the reference polypeptide or polynucleotide. For example, these differences include substitutions, insertions, deletions or any desired combinations of such changes in a reference polypeptide or polypeptide. Polypeptide and protein variants can further consist of changes in charge and/or post-translational modifications (such as glycosylation, methylation. phosphorylation, etc.). When the term "variant" is used in reference to a microorganism, it typically refers to a strain microbial strain having identifying characteristics of the species to which it belongs, while having at least one nucleotide sequence variation or identifiably different trait with respect to the parental strain, where the trait is genetically based (heritable). For example, for a *Nannochloropsis* strain, identifiable traits include the lack of chlorophyll b and c, which is different from other related microalgae.

A "vector" is any genetic element capable of serving as a vehicle of genetic transfer, expression, or replication for a foreign polynucleotide in a host cell. For example, a vector may be an artificial chromosome or a plasmid, and may be capable of stable integration into a host cell genome, or it may exist as an independent genetic element (e.g., episome, plasmid). A vector may exist as a single polynucleotide or as two or more separate polynucleotides. Vectors may be single copy vectors or multicopy vectors when present in a host cell. Preferred vectors for use in the present invention are expression vector molecules in which one or more functional genes can be inserted into the vector molecule, in proper orientation and proximity to expression control elements resident in the expression vector molecule so as to direct expression of one or more proteins when the vector molecule resides in an appropriate (e.g. homologous) host cell.

All publications and patent applications mentioned in this specification are herein incorporated by reference to the same extent as if each individual publication or patent application was specifically and individually indicated to be incorporated by reference.

No admission is made that any reference constitutes prior art. The discussion of the references states what their authors assert, and the applicants reserve the right to challenge the accuracy and pertinence of the cited documents. It will be clearly understood that, although a number of prior art publications are referred to herein; this reference does not constitute an admission that any of these documents forms part of the common general knowledge in the art.

The discussion of the general methods given herein is intended for illustrative purposes only. Other alternative methods and embodiments will be apparent to those of skill in the art upon review of this disclosure.

Nucleic Acid Molecules

The present disclosure constitutes the first description of *Nannochloropsis* SLs and their utility for engineering Eustigmayophytes, and even other classes within the stramenopile lineage. The heterokont SL sequences of the present invention were identified as sequences occurring in the 5' region of *Nannochloropsis* cDNAs while being absent from the genome locus corresponding to the protein-encoding portion of the cDNAs. Thus, in one aspect of the present invention, the disclosure provides novel isolated nucleic acid molecules that include the SL sequences and sequences homologous thereto. Additional embodiments of the present application further include recombinant nucleic acid molecules, such as recombinant constructs, expression cassettes and nucleic acid vectors, which comprise a nucleic acid molecule as disclosed herein. In addition, the nucleic acid molecules according to the present invention may be present in a chimeric, modular, or hybrid nucleic acid molecule. The nucleic acid molecules of the present invention will typically be "biologically active" with respect to either a structural attribute, such as the capacity of a nucleic acid molecule to hybridize to another nucleic acid molecule, or the ability of a polynucleotide sequence to be recognized and bound by a transcription or translation factor or a ribosome (or to compete with another nucleic acid molecule for such binding).

In one aspect, the present invention provides isolated or recombinant nucleic acid molecules in which the isolated or recombinant nucleic acid molecules comprise a nucleic acid sequence, referred to herein as an SL-homologous sequence, having at least 80%, such as at least 85%, at least 86%, at least 87%, at least 88%, about 89%, at least 90%, at least 91%, at least 92%, for example, at least 93%, at least 94%, at least 95%, or 100% sequence identity to a nucleic acid sequence selected from the group consisting of SEQ ID NO:1, SEQ ID NO:2, SEQ ID NO:3, SEQ ID NO:4, SEQ ID NO:5, SEQ ID NO:6, and a complement of any thereof. In some examples, an isolated or recombinant nucleic acid molecule comprises a nucleic acid sequence having at least 80%, at least 83%, at least 85%, at least 86%, at least 87%, at least 88%, about 89%, at least 90%, at least 91%, at least 92%, at least 93%, at least 94%, at least 95%, or 100% sequence identity to a nucleic acid sequence selected from the group consisting of SEQ ID NO:2, SEQ ID NO:3, and SEQ ID NO:4. Alternatively or in addition, an isolated or recombinant nucleic acid molecule comprises a nucleic acid sequence having at least 80%, at least 83%, at least 85%, at least 86%, at least 87%, at least 88%, about 89%, at least 90%, at least 91%, at least 92%, at least 93%, at least 94%, at least 95%, or 100% sequence identity to a nucleic acid sequence selected from the group consisting of SEQ ID NO:5 and SEQ ID NO:6. In some examples, an isolated or recombinant nucleic acid molecule comprises a nucleic acid sequence selected from the group consisting of SEQ ID NO:2, SEQ ID NO:3, and SEQ ID NO:4. The isolated or recombinant nucleic acid molecules may be nucleic acid molecules of less than or equal to 250 nucleotides, less than or equal to 200 nucleotides, less than or equal to 180 nucleotides, less than or equal to 150 nucleotides, less than or equal to 120 nucleotides, and may be an oligonucleotide, used herein to denote a nucleic acid molecule of less than or equal to 100 nucleotides, and can be less than or equal to 80 nucleotides, less than or equal to about 65 nucleotides in length, less than or equal to about 50 nucleotides, less than or equal to about 40 nucleotides in length, less than or equal to about 30 nucleotides in length, or less than or equal to about 22 nucleotides in length. The isolated or recombinant nucleic acid molecule of less than or equal to 250 nucleotides in length can be double-stranded or single-stranded. In some instances, the nucleic acid molecule can be partially double-stranded and partially single-stranded.

In some examples, the isolated or recombinant nucleic acid molecule of less than or equal to 250 nucleotides in length is a DNA molecule, and can be, for example a DNA oligonucleotide of 100 nucleotides or less. The isolated or recombinant nucleic acid molecule of less than or equal to 250 nucleotides in length can in some examples include, in addition to an SL-homologous sequence, one or more sequences that facilitate cloning, such as, for example, restriction endonuclease recognition sites, topoisomerase binding site, or regions of homology with another nucleic acid molecule, such as, for example, a cloning vector. The isolated or recombinant nucleic acid molecule of less than or equal to 250 nucleotides in length can in some examples include a SL-homologous nucleic acid sequence having at least 80%, for example at least 83%, at least 85%, at least 86%, at least 87%, at least 88%, about 89%, at least 90%, at least 91%, at least 92%, at least 93%, at least 94%, at least 95%, or 100% sequence identity to a nucleic acid sequence selected from the group consisting of SEQ ID NO:2, SEQ ID NO:3, and SEQ ID NO:4. Alternatively or in addition, the isolated or recombinant nucleic acid molecule of less than or equal to 250 nucleotides in length can in some examples include a SL-homologous nucleic acid sequence according to SEQ ID NO:5 or SEQ ID NO:6. For example, the SL-homologous nucleic acid sequence can be or comprise a nucleic acid sequence selected from the group consisting of SEQ ID NO:2, SEQ ID NO:3, and SEQ ID NO:4.

Alternatively or in addition, an isolated or recombinant nucleic acid molecule, as provided herein can be a nucleic acid sequence can be having at least 80%, for example at least 83%, at least 85%, at least 87%, at least 88%, about 89%, at least 90%, at least 91%, at least 92%, at least 93%, at least 94%, at least 95%, or 100% sequence identity to a nucleic acid sequence selected from the group consisting of SEQ ID NO:1, SEQ ID NO:2, SEQ ID NO:3, SEQ ID NO:4, SEQ ID NO:5, SEQ ID NO:6 and a complement of any thereof operably linked to a heterologous nucleic acid, where the heterologous nucleic acid molecule can be 1) a regulatory sequence; or 2) a protein-encoding sequence, where the protein-encoding sequence is from a species other than the species the SL sequence is derived from. A regulatory sequence can be, as nonlimiting examples, a promoter or enhancer sequence that promotes or regulates transcription. To be in operable linkage, the SL-homologous sequence and the heterologous regulatory sequence or heterologous protein-encoding sequence need not directly abut, but can in some examples be separated by from one to about 500 nucleotides, for example, from one to about 300 nucleotides, from one to, about 100 nucleotides, or from one to about 50 nucleotides. The isolated or recombinant nucleic acid molecule comprising a SL-homologous nucleic acid sequence operably linked to a heterologous sequence can have at least 80%, for example at least 83%, at least 85%, at least 86%, at least 87%, at least 88%, about 89%, at least 90%, at least 91%, at least 92%, at least 93%, at least 94%, at least 95%, or 100% sequence identity to a nucleic acid sequence selected from the group consisting of SEQ ID NO:2, SEQ ID NO:3, and SEQ ID NO:4. Alternatively or in addition, the isolated or recombinant nucleic acid molecule comprising a SL-homologous nucleic acid sequence operably linked to a heterologous sequence can in some examples include a SL-homologous nucleic acid sequence according to SEQ ID NO:5 or SEQ ID NO:6. For example, the SL-homologous nucleic acid sequence can be or comprise a nucleic acid sequence selected from the group consisting of SEQ ID NO:2, SEQ ID NO:3, and SEQ ID NO:4.

The present invention provides nucleic acid constructs for the expression of protein-encoded genes comprising an SL-homologous nucleic acid sequence of the invention operably linked to a heterologous promoter. Such nucleic acid molecules can comprise a SL-homologous sequence that is operably linked to a heterologous promoter positioned 5' ("upstream") of the SL-homologous sequence. A "heterologous promoter" in this context is a promoter not operably linked to the SL sequence in the genome of the organism from which the SL-homologous sequence is derived, i.e., the heterologous is any promoter that is not operably linked to the gene encoding the SL RNA that contributes or "donates" the spliced leader to another RNA transcript in the organism that naturally includes the SL sequence. The heterologous promoter can be any promoter and can be, as non-limiting examples, a fungal, plant, heterokont, or algal promoter. In some examples, the promoter is a promoter from a Eustigmatophyte species, such as, for example, a species of *Nannochloropsis, Eustigmatos, Monodus,* or *Vischeria*. In some examples, the promoter is a *Nannochloropsis* promoter. Nonlimiting examples of *Nannochloropsis* promoters include those disclosed in U.S. Pat. No. 8,318,482; U.S. Patent Appl. Pub. No. US 2013/0023035; U.S. patent application Ser. No. 13/486,930, filed Jun. 1, 2012; and U.S. patent application Ser. No. 13/915,522, filed Jun. 11, 2013, all of which are incorporated herein by reference. The heterologous promoter and SL-homologous sequence can directly abut one another or can be separated by, for example, from 0 to 1000 nucleotides that can optionally be derived from the 5' region of a naturally-occurring gene. For example, the heterologous promoter and SL-homologous sequence can be separated by up to about 500 nucleotide, up to about 350 nucleotides, up to about 250 nucleotides, up to about 100 nucleotides, up to about 50 nucleotides, up to about 30 nucleotides, up to about 20 nucleotides, or up to about 10 nucleotides. The nucleic acid molecule that comprises a SL-homologous sequence operably linked to a heterologous promoter can be designed for cloning of a protein-encoding sequence downstream of the SL-homologous sequence, for example, the construct can includes a restriction endonuclease recognitions site, polylinker, or sequences for topoisomerase or recombinational cloning downstream of the SL-homologous sequence.

The present invention also provides nucleic acid constructs for the expression of protein-encoded genes comprising an SL-homologous nucleic acid sequence of the invention operably linked to a heterologous protein-encoding sequence. Such nucleic acid molecules can comprise a SL-homologous sequence that is operably linked to a heterologous protein-encoding sequence positioned 3' ("downstream") of the SL-homologous sequence. A "heterologous protein-encoding sequence" in this context is a protein-encoding sequence that is not 100% identical to a protein-encoding sequence of the species in which the SL sequence naturally occurs, and can be a protein-encoding sequence of a species other than the species the SL is derived from, i.e., a gene that is not naturally associated with the spliced leader sequence. The SL-homologous sequence and heterologous protein-encoding sequence can directly abut one another or can be separated by, for example, from 0 to 1000 nucleotides that can optionally be derived from the 5' UTR of a naturally-occurring gene. For example, the SL-homologous sequence can be separated from a heterologous protein-encoding sequence by up to about 850 nucleotide, up to about 750 nucleotides, up to about 500 nucleotides, up to about 350 nucleotides, up to about 250 nucleotides, up to about 200 nucleotides, up to about 150 nucleotides, up to about 100 nucleotides, up to about 50 nucleotides, up to about 30 nucleotides, or up to about 20 nucleotides. The nucleic acid molecule that comprises a SL-homologous sequence operably linked to a heterologous protein-encoding sequence can also include a promoter positioned upstream of the SL-homologous sequence. The promoter can be any promoter, including but not limited to any of those disclosed above.

Thus, the invention also encompasses expression cassettes, vectors, as well as methods for the introduction of exogenous DNA into cells with concomitant expression of the exogenous DNA in the cells such as those described herein and in the art, for example, in Sambrook et al. (2001, *Molecular Cloning: A Laboratory Manual*, Cold Spring Harbor Laboratory, New York). In some embodiments, the present invention provides expression cassettes comprising SEQ ID NOs: 1, 2, 3, 4, 5, or 6, or variants thereof having at least 80%, for example at least 83%, at least 85%, at least 86%, at least 87%, at least 88%, about 89%, such as at least 90%, at least 91%, at least 92%, at least 93%, at least 94%, at least 95%, or 100% sequence identity to SEQ ID NOs: 1, 2, 3, 4, 5, or 6 operably linked to a promoter and/or a protein-encoding sequence. In some embodiments, such expression cassettes can be provided in a number of types of vectors. However, the present invention should not be construed to be limited to any particular vector. Instead, the present invention should be construed to encompass a wide plethora of vectors which are readily available and/or well-known in the art.

Without limiting the invention to any particular mechanism, an SL-homologous sequence as disclosed herein may enhance expression of a recombinant coding sequence to which the SL sequence is operably linked. It can be appreciated that the SL sequence tag of the invention on an expression cassette may enhance expression of one or more recombinant proteins whether encoded on separate corresponding genes or encoded on a single polycistronic gene present on the expression vector, where an SL sequence may precede one or multiple coding sequences of a polycistronic gene. The SL sequence tag may be used to enhance the level of expression of a recombinant protein using both stable expression systems and transient expression system.

Nucleic acid molecules or fragments thereof of the present invention encompass those exhibiting substantial sequence identities to the nucleic acid sequences disclosed herein. As used herein "sequence identity" refers to the extent to which two optimally aligned polynucleotide are invariant throughout a window of alignment of components, e.g., nucleotides. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

"Percentage of sequence identity," as used herein, is determined by comparing two optimally locally aligned sequences over a comparison window defined by the length of the local alignment between the two sequences. The nucleotide sequence in the comparison window may comprise additions or deletions (e.g., gaps or overhangs) as compared to the reference sequence (which does not comprise additions or deletions) for optimal alignment of the two sequences. Local alignment between two sequences only includes segments of each sequence that are deemed to be sufficiently similar according to a criterion that depends on the algorithm used to perform the alignment (e.g. BLAST). The percentage identity is calculated by determining the number of positions at which the identical nucleic acid base occurs in both sequences to yield the number of matched positions, dividing the number of matched positions by the total number of positions in the window of comparison and multiplying the result by 100. Optimal alignment of sequences for comparison may be conducted by the local homology algorithm of Smith and Waterman (*Add. APL. Math.* 2:482, 1981), by the global homology alignment algorithm of Needleman and Wunsch (*J. Mol. Biol.* 48:443, 1970), by the search for similarity method of Pearson and Lipman (*Proc. Natl. Acad. Sci. USA* 85: 2444, 1988), by heuristic implementations of these algorithms (NCBI BLAST, WU-BLAST, BLAT, SIM, BLASTZ), or by inspection.

Given that two sequences have been identified for comparison, GAP and BESTFIT programs are typically employed to determine their optimal alignment. For this purpose, the percent of sequence identity is typically determined using the BESTFIT or GAP program of the Sequence Analysis Software Package™ (Version 10; Genetics Computer Group, Inc., Madison, Wis.). GAP utilizes the algorithm of Needleman and Wunsch (Needleman and Wunsch, *J. Mol. Biol.* 48:443-453, 1970) to find the alignment of two sequences that maximizes the number of matches and minimizes the number of gaps. BESTFIT performs an optimal alignment of the best segment of similarity between two sequences and inserts gaps to maximize the number of matches using the local homology algorithm of Smith and Waterman (Smith and Waterman, *Adv. Applied Math.,* 2:482-489, 1981, Smith et al., *Nucl. Acids Res.* 11:2205-2220, 1983). The percent identity is most typically determined using the BESTFIT program. Typically, the default values of 5.00 for gap weight and 0.30 for gap weight length are used. The term "substantial sequence identity" between polynucleotide sequences refers to polynucleotide comprising a sequence that has at least 50% sequence identity, typically at least 60%, at least 65%, at least 70%, at least 75%, at least 80%, for example, at least 85%, at least 90%, at least 95%, or at least 96%, 97%, 98% or 99% sequence identity compared to a reference sequence using the programs. Thus, according to one embodiment of the invention are polynucleotide molecules comprising sequences that have at least 50% sequence identity, for example at least 60%, at least 65%, at least 70%, at least 75%, at least 80%, such as at least 85%, at least 90%, or at least 95% sequence identity with a polynucleotide sequence described herein. Polynucleotide molecules that are capable of enhancing expression of operably linked polynucleotide molecules and have a substantial percent sequence identity to the polynucleotide sequences of the polynucleotide molecules provided herein are encompassed within the scope of this invention.

As used herein, "sequence homology" refers to the level of similarity between two or more nucleic acid sequences in terms of percent of positional identity (i.e., sequence similarity or identity). In some instances, the term "homology" also refers to the concept of similar functional properties among different nucleic acids. In addition, pairwise sequence homology or sequence similarity, as used herein refers to the percentage of residues that are similar between two sequences aligned. As such, the term "homologous", as applied to nucleic acid molecules, denotes a characteristic of a nucleic acid sequence, in which a nucleic acid sequence has at least about 60% sequence identity as compared to a reference sequence, for example, %, at least 65%, at least 70%, at least 75%, or at least 80%, at least 85%, at least 90%, at least 93%, at least 94%, at least 95%, or at least 96%, 97%, 98% or 99% sequence identity as compared to a reference sequence. In some instances, an SL-homologous sequence can have 100% or 100% identity to an identified naturally-occurring SL sequence.

In some embodiments, nucleic acid molecules of the present invention are between about 0.01 Kb and about 50 Kb, between about 0.015 Kb and about 0.05 Kb, or between about 0.02 Kb and about 0.1 Kb, for example between about 0.02 Kb and about 0.2 Kb, or between about 0.1 Kb and about 1 Kb, between about 0.5 Kb and about 2 Kb, between about 1 Kb and about 5 Kb, about 2 Kb and about 10 Kb, about 2 Kb and about 5 Kb, between about 5 Kb and about 10 Kb, about 5 Kb and about 20 Kb, about 10 Kb and about 20 Kb, or about 20 Kb and about 50 Kb in length.

A nucleic acid molecule can be produced using a number of methods known to those skilled in the art (see, for example, Sambrook et al., In: *Molecular Cloning, A Laboratory Manual,* 2nd Edition, Cold Spring Harbor Press, Cold Spring Harbor, N.Y. 1989). Typically, an isolated nucleic acid molecule of the present invention is produced using recombinant DNA technology (e.g., polymerase chain reaction (PCR) amplification, cloning, etc.), chemical synthesis, or a combination thereof. Isolated nucleic acid molecules of the present invention include sequences of natural nucleic acid molecules and homologs thereof, including, but not limited to, natural allelic variants and modified nucleic acid molecules in which nucleotides have been inserted, deleted, and/or substituted. For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. The nucleic acid molecule can comprise DNA or RNA, or can be or include a peptide nucleic acid (PNA). In particular examples, the nucleic acid molecule is a DNA molecule.

A nucleic acid molecule as provided herein can optionally comprise or be conjugated to one or more detectable labels, specific binding members, polymers, peptides, polypeptides, additional nucleic acids, carbohydrates, lipids, steroids, enzymes, small molecules, protecting groups, or coupling agents. Oligonucleotide probes and primers of the present invention can also be coupled to linkers that are in turn coupled to detectable labels, specific binding members, polymers, small molecules, matrices, polymers, and the like. Examples of fluorescent labels that can be incorporated into nucleotides of the nucleic acid molecules provided herein include, but are not limited to: DEAC, CB, Cy3.5, Cy5.5, DEAC, CB, Cy3.5, Cy5.5, R6G, TAMRA, TxR, OG, A488, Cy3, Cy5, AMCA, FITC, BIO, DIG, and 1DNP. Radionucleotides that may be incorporated into a nucleic acid molecule as provided herein include, without limitation, $^{32}P$, $^{33}P$, and $^{35}S$. Alternatively or in addition, a nucleic acid molecule as provided herein can include a small molecule or hapten that can be recognized by a binding partner such as a protein that binds the small molecule or hapten or an antibody. A binding protein or antibody can be directly or indirectly labeled for detection of the nucleic acid molecule. Examples of haptens and small molecules that can be incorporated into a nucleic acid molecule as provided herein include, without limitation, biotin, digoxigenin, dinitrophenol, and fluorescein. Alternatively or in addition to any of the above labels and binding moieties, a nucleic acid molecule as provided herein can be bound to a solid support, such as, without limitation, a glass slide, membrane, filter, solid surface, chip, or array comprising plastic, glass, silicon, a polymer or metal, or other suitable material, or a bead, column matrix, etc.

Recombinant Host Cell

In certain embodiments, the present disclosure provides recombinant host cells comprising an isolated or recombinant nucleic acid molecule as disclosed herein. In particular examples, a recombinant host cell as provided herein includes an isolated or recombinant nucleic acid molecule as provided herein that comprises an SL-homologous nucleic acid sequence having at least 80%, for example at least 85%, at least 86%, at least 87%, at least 88%, such as about 89%, at least 90%, at least 91%, at least 92%, at least 93%, at least 94%, at least 95%, or 100% sequence identity to a nucleic acid sequence selected from the group consisting of SEQ ID NO:1, SEQ ID NO:2, SEQ ID NO:3, SEQ ID NO:4, SEQ ID NO:5, SEQ ID NO:6, and a complement of any thereof. The SL-homologous sequence is operably linked to a heterologous nucleic acid, e.g., a protein-encoding sequence that is not derived from the same species as the spliced leader sequence. For example, where the host cell is of a *Nannochloropsis* species, the protein encoding sequence may not be derived from a *Nannochloropsis* species.

In various examples, a recombinant host cell as provided herein includes an SL-homologous sequence operably linked to a regulatory element and/or a coding sequence for a polypeptide of interest that is not derived from the host strain, e.g., is a gene not derived from a *Nannochloropsis* species. In certain examples, the regulatory element comprises a promoter. In some other examples, the polypeptide of interest is involved in the production of one or more biomolecules, such as, without limitation, a lipid, a terpenoid, a polyketide, a protein, a peptide, one or more amino acids, a carbohydrate, an alcohol, a nucleic acid, one or more nucleotides, nucleosides, or nucleobases, a vitamin, a cofactor, a hormone, an antioxidant, or a pigment or colorant. In some preferred embodiments, the recombinant host cell can exhibit higher expression level of the polypeptide of interest than is exhibited by a control cell substantially identical to the recombinant host cell. For example, expression of the polypeptide of interest can result in the recombinant host cell producing a greater amount of biomass or a greater amount of one or more aforementioned biomolecules.

A host cell that includes a nucleic acid molecule as provided herein that can include an SL sequence operably linked to a protein-encoding sequence that may confer any desirable trait, such as, but not limited to, increased production of biomolecules of interest, such as one or more proteins, pigments, alcohols, or lipids. For example, for production of lipid, a host cell (such as but not limited to an algal or heterokont host cell) can optionally include one or more non-native genes encoding polypeptides that functions in lipid biosynthesis, including, but not limited to, polypeptides that encode enzymes for the production of fatty acids, fatty acid derivatives, and/or glycerolipids including, but not limited to, diacylglycerol acyltransferase (DGAT) gene, a glycerolphosphate acyltransferase (GPAT) gene, a lysophosphatidic acid acyltransferase (dehydrogenase) (LPAAT) gene, a phosphatidic acid phosphatase (PAP) gene, and/or a monoacylglycerol acyltransferase (MGAT) gene.

In principle, the methods and compositions according to the present invention can be deployed for genetic engineering of any microbial species, including, but not limited to, microalgae, microbial heterokonts, and microfungi. The methods and compositions are typically used with microorganisms that are important or interesting for aquaculture, agriculture, for the production of biomass used in production of liquid fuel molecules and other chemicals. Suitable species may include members of the genera *Amphora, Ankistrodesmus, Aplanochytrium, Asteromonas, Boekelovia, Bolidomonas, Borodinella, Botrydium, Botryococcus, Bracteococcus, Carteria, Chaetoceros, Chlamydomonas, Chlorella, Chlorococcum, Chlorogonium, Chrococcidiopsis, Chroomonas, Chrysophyceae, Chrysosphaera, Colwellia, Cricosphaera, Oypthecodinium, Cryptococcus, Cryptomonas, Cunninghamella, Cyclotella, Desmodesmus, Dunaliella, Elina, Ellipsoidon, Emiliania, Eremosphaera, Ernodesmius, Euglena, Eustigmatos, Fragilaria, Fragilariopsis, Franceia, Gloeothamnion, Haematococcus, Hantzschia, Heterosigma, Hymenomonas, Isochrysis, Japanochytrium, Labrinthula, Labyrinthomyxa, Labyrinthula, Lepocinclis, Micractinium, Monodus, Monoraphidium, Moritella, Mortierella, Mucor, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phaeodactylum, Phagus, Pichia, Picochlorum, Pithium, Platymonas, Pleurochrysis, Pleurococcus, Porphyridium, Prototheca, Pseudochlorella, Pseudoneochloris, Pseudostaurastrum, Pyramimonas, Pyrobotrys, Rhodosporidium, Scenedesmus, Schizochlamydella, Schizochytrium, Skeletonema, Spirulina, Spyrogyra, Stichococcus, Tetrachlorella, Tetraselmis, Thalassiosira, Thraustochytrium, Tribonema, Ulkenia, Vaucheria, Vibrio, Viridiella, Vischeria,* and *Volvox.*

In some embodiments of the present application, microorganisms for genetic modification or nucleic acid isolation include photosynthetic organisms such as microalgae, diatoms, and the like. In some examples, heterokont species considered for use in the invention include, but are not limited to, species of the taxonomic groups Bacillariophytes (diatoms), Eustigmatophytes, Labrinthulids, and Thraustochytrids. In some examples, a strain used in the invention may be a species of Labrinthulid or Thraustochytrid such as *Labryinthula, Labryinthuloides, Thraustochytrium, Schizochytrium, Aplanochytrium, Aurantiochytrium, Japonochytrium, Diplophrys*, or *Ulkenia*.

Exemplary diatoms may include members of the genera *Achnanthes, Amphora, Chaetoceros, Coscinodiscus, Cylindrotheca, Cyclotella, Cymbella, Hantzschia, Navicula, Nitzschia, Pavlova, Pseudo-Nitzschia, Phaeodactylum, Psammodictyon, Skeletonema, Thalassionema*, and *Thallasiosira*. Eustigmatophytes that can be used for genetic modification or nucleic acid isolation include, for example, species of *Eustigmatos, Monodus, Nannochloropsis*, and *Vischeria*.

For example, microorganisms for genetic modification or nucleic acid isolation as disclosed herein include members of the genus *Nannochloropsis*. Particularly suitable species include *N. gaditana, N. granulata, N. limnetica, N. maritime, N. oceanica, N. oculata*, and *N. salina*. Preferred species within the genus *Nannochloropsis* include, but are not limited to, *N. gaditana, N. oceanica, N. oculata*, and *N. salina*.

One skilled in the art will appreciate that a number of transformation methods can be used for genetic transformation of microorganisms and, therefore, can be deployed for the methods of the present invention. "Stable transformation" is intended to mean that the nucleic acid construct introduced into an organism integrates into the genome of the organism or is part of a stable episomal construct and is capable of being inherited by the progeny thereof. "Transient transformation" is intended to mean that a polynucleotide is introduced into the organism and does not integrate into the genome or otherwise become established and stably inherited by successive generations.

Genetic transformation can result in stable insertion and/or expression of transgenes from either the nucleus or the plastid, and in some cases can result in transient expression of transgenes. For example, genetic transformation of microalgae has been reported successful for more than 30 different strains of microalgae, which belong to at least ~22 species of green, red, and brown algae, diatoms, euglenids, and dianoflagellates (see, e.g., Radakovits et al., *Eukaryotic Cell*, 2010; and Gong et al., *J. Ind. Microbiol. Biotechnol.*, 2011). Non-limiting examples of such useful transformation methods include agitation of cells in the presence of glass beads or silicon carbide whiskers as reported by, for example, Dunahay, *Biotechniques*, 15(3):452-460, 1993; Kindle, *Proc. Natl. Acad. Sci. U.S.A.*, 1990; Michael and Miller, *Plant J.*, 13, 427-435, 1998. Electroporation techniques have been successfully used for genetic transformation of several microalgal species including *Nannochloropsis* sp. (see, e.g., Chen et al., *J. Phycol.*, 44:768-76, 2008), *Chlorella* sp. (see, e.g., Chen et al., *Curr. Genet.*, 39:365-370, 2001; Chow and Tung, *Plant Cell Rep.* Vol. 18, No. 9, 778-780, 1999), *Chlamydomonas* (Shimogawara et al., *Genetics*, 148: 1821-1828, 1998), *Dunaliella* (Sun et al., *Mol. Biotechnol.*, 30(3): 185-192, 2005). Microprojectile bombardment, also referred to as microparticle bombardment, gene gun transformation, or biolistic bombardment, has been used successfully for several algal species including, for example, diatoms species such as *Phaeodactylum* (Apt et al., *Mol. Gen. Genet.*, 252:572-579, 1996), *Cyclotella* and *Navicula* (Dunahay et al., *J. Phycol.*, 31:1004-1012, 1995), *Cylindrotheca* (Fischer et al., *J. Phycol.*, 35:113-120, 1999), and *Chaetoceros* sp. (Miyagawa-Yamaguchi et al., *Phycol. Res.* 59: 113-119, 2011), as well as green algal species such as *Chlorella* (El-Sheekh, *Biologia Plantarum*, Vol. 42, No. 2: 209-216, 1999), and *Volvox* species (Jakobiak et al., *Protist*, 155:381-93, 2004). Additionally, *Agrobacterium*-mediated gene transfer techniques can also be useful for genetic transformation of microalgae, as has been reported by, for example, Kumar, *Plant Sci.*, 166(3):731-738, 2004, and Cheney et al., *J. Phycol.*, Vol. 37, Suppl. 11, 2001.

A transformation vector as described herein will typically comprise a marker gene that confers a selectable or scorable phenotype on target host cells, e.g., algal cells. A number of selectable markers have been successfully developed for efficient isolation of genetic transformants of algae. Common selectable markers include antibiotic resistance, fluorescent markers, and biochemical markers. Several different antibiotic resistance genes have been used successfully for selection of microalgal transformants, including blastocydin, bleomycin (see, for example, Apt et al., 1996, supra; Fischer et al., 1999, supra; Fuhrrnann et al., *Plant J.*, 19, 353-61, 1999, Lumbreras et al., *Plant J.*, 14(4):441-447, 1998; Zaslayskaia et al., *J. Phycol.*, 36:379-386, 2000), spectinomycin (Cerutti et al., *Genetics*, 145: 97-110, 1997; Doetsch et al., *Curr. Genet.*, 39, 49-60, 2001; Fargo, *Mol. Cell. Biol.*, 19:6980-90, 1999), streptomycin (Berthold et al., *Protist*, 153:401-412, 2002), paromomycin (Jakobiak et al., *Protist*, supra.; Sizova et al., *Gene*, 277:221-229, 2001), nourseothricin (Zaslayskaia et al., 2000, supra), G418 (Dunahay et al., 1995, supra; Poulsen and Kroger, *FEBS Lett.*, 272:3413-3423, 2005, Zaslayskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, *Mol. Gen. Genet.* 263:404-10, 2000), zeomycin and phleomycin (e.g., ZEOCIN™ pheomycin D1) resistance (Stevens, *Mol. Gen. Genet.* 251:23-30, 1996), and paramomycin and neomycin resistance (Sizova et al., 2001, supra). Other fluorescent or chromogenic markers that have been used include luciferase (Falciatore et al., *J. Mar. Biotechnol.*, 1: 239-251, 1999; Fuhrmann et al., *Plant Mol. Biol.*, 2004; Jarvis and Brown, *Curr. Genet.*, 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.*, 1:165-169, 1994), β-galactosidase (Gan et al., *J. Appl. Phycol.*, 15:345-349, 2003; Jiang et al., *Plant Cell Rep.*, 21:1211-1216, 2003; Qin et al., *High Technol. Lett.*, 13:87-89, 2003), and green fluorescent protein (GFP) (Cheney et al., 2001, supra; Ender et al., *Plant Cell*, 2002, Franklin et al., *Plant J.*, 2002; 56, 148, 210).

One skilled in the art will readily appreciate that a variety of known promoter sequences can be usefully deployed for transformation systems of microalgal species in accordance with the present invention. For example, the promoters commonly used to drive transgene expression in microalgae include various versions of the of cauliflower mosaic virus promoter 35S (CaMV35S), which has been used in both dinoflagellates and chlorophyta (Chow et al, *Plant Cell Rep.*, 18:778-780, 1999; Jarvis and Brown, *Curr. Genet.*, 317-321, 1991; Lohuis and Miller, *Plant J.*, 13:427-435, 1998). The SV40 promoter from simian virus has also reported to be active in several algae (Gan et al., *J. Appl. Phycol.*, 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.*, 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/β2TUB (tubulin) (Schroda et al., *Plant J.*, 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of an fcp gene encoding a diatom fucoxanthin-chlorophyll a/b binding protein (Falciatore et al., *Mar. Biotechnol.*, 1:239-251, 1999; Zaslayskaia et al., *J. Phycol.* 36:379-386, 2000) or the vcp gene encoding a eustigmatophyte violaxanthin-chlorophyll a/b binding protein (see U.S. Pat. No. 8,318,482). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, *FEBS Lett* 272: 3413-3423, 2005), thus gene expression can be switched off or on when microalgal cells are grown in the presence of ammonium/nitrate. Other regulatable promoters from *Nannochloropsis* include those disclosed in U.S. Patent Appl. Pub. No. US 2013/0023035. Additional algal promoters that can find use in the constructs and transformation systems provided herein include those disclosed in U.S. patent application Ser. No. 13/486,930, filed Jun. 1, 2012; U.S. patent application Ser. No. 13/693,585, filed Dec. 4, 2012; and U.S. patent application Ser. No. 13/915,522, filed Jun. 11, 2013, all incorporated by reference herein.

Methods for Enhancing Gene Expression

One aspect of the present invention concerns methods of enhancing production of a desired gene product. In particular, the methods of the invention involve enhancing the expression of the product by enhancing translation of messenger RNA derived from the structural gene.

The methods may be based on any of the reported roles of spliced leader sequences in enhancing gene expression, e.g. (i) increasing the stability of mature transcripts, (ii) enabling or enhancing the transport of mature transcripts out of the nucleus to the cytoplasm, and (iii) facilitating the assembly of complete ribosome with large and small subunits at the AUG initiation codon, thereby allowing efficient translation.

In some examples of this aspect, a transgene of interest is operably linked to a SL sequence as provide herein in an expression cassette, such that the gene of interest is positioned downstream of the SL sequence of the present invention. Optionally, a heterologous promoter is positioned upstream of the SL sequence. In one preferred embodiment, the expression cassette comprises the following operably linked elements: a promoter, a SL sequence of the invention, and a coding sequence of interest.

Such expression cassette, in which a transgene of interest is operably linked to an SL sequence of the present invention, can be then transformed into a host cell and expressed. In some particular embodiments, the transgene of interest (which in some instances is not derived from a *Nannochloropsis* species) may optionally be linked to a nucleotide sequence having at least 80%, for example at least 83%, at least 85%, at least 86%, at least 87%, at least 88%, such as about 89%, at least 90%, at least 91%, at least 92%, at least 93%, at least 94%, at least 95%, or 100% sequence identity to a nucleic acid sequence selected from the group consisting of SEQ ID NO:1, SEQ ID NO:2, SEQ ID NO:3, SEQ ID NO:4, SEQ ID NO:5, SEQ ID NO:6 and a complement of any thereof. For example, the transgene of interest may be linked to a nucleic acid having at least 80%, for example at least 83%, at least 85%, at least 86%, at least 87%, at least 88%, such as about 89%, at least 90%, at least 91%, at least 92%, at least 93%, at least 94%, at least 95%, or 100% sequence identity to a nucleic acid sequence selected from the group consisting of SEQ ID NO:2, SEQ ID NO:3, and SEQ ID NO:4. Alternatively or in addition, the transgene of interest may be linked to a nucleic acid according to SEQ ID NO:5 or SEQ ID NO:6.

In principle, an expression cassette as provided herein is applicable to any situation where it is desirable to enhance expression of a desired coding sequence. In some instances, the expression cassette is useful for enhancing expression over their wild-type counterparts or otherwise a coding sequence that is not operably linked to a SL sequence of the invention.

In some aspects, the methods of the invention are for the production of a heterologous gene product by the expression of the gene encoding the desired product (i.e. by the expression of a heterologous gene), thus concerning methods of recombinant gene expression. As noted above, methods of recombinant gene expression are well known in the art and have been used industrially or commercially for the production of proteins. A variety of different expression systems are known and may be used to express the gene according to the present invention i.e. as the basis for the present invention. At its most basic, an expression system includes a promoter for expression of the desired gene and the gene it is desired to express, or a site for insertion of the desired gene, such that it may be expressed under the control of the promoter. According to the present invention, the expression system also includes a heterologous spliced leader positioned downstream of the promoter. Also included may be other transcriptional or translational control elements necessary or desirable to achieve or optimize expression, as discussed further elsewhere herein.

Accordingly, the expression system which is used to produce the desired gene product whose expression is enhanced can be any system from which a gene can be expressed i.e. any system for the expression of a gene, for example for the expression of a recombinant gene. The expression system may be an in vivo or in vitro system and may for example be a vector e.g. a plasmid or an artificial chromosome or a viral vector, or a construct (e.g. expression cassette) for insertion into a vector. The vector may be autonomously replicating or designed for chromosomal integration (e.g. a transposon-based vector or with sites for specific or homologous recombination for integration into the chromosome of the host cell into which the vector is introduced). A vector may be introduced into a host cell, and the host cell may be grown or cultured to allow said gene to be expressed, e.g. under conditions which allow the gene to be expressed.

Methods for Identifying and/or Isolating Nucleic Acid Molecules

In another aspect of the invention, the SL sequences and their prevalence in heterokont mRNAs can be used to identify and/or isolate nucleic acid molecules, e.g. mature mRNAs or cDNAs that include a 5' SL sequence tag as disclosed herein.

Accordingly, the present invention also provides a method for identifying and/or isolating one or more nucleic acid molecules from a population of nucleic acid molecules. The identifying or isolating methods disclosed herein can comprise hybridizing a nucleic acid molecule as disclosed herein that comprises an SL-homologous sequence with a population of nucleic acid molecules, which can be derived from a cell or cell culture. The cell can optionally be in a mixed cell culture, i.e., a culture that includes more than one species of microorganism. The cell or cell culture in some examples is a *Nannochloropsis* cell or a cell culture that comprises at least one *Nannochloropsis* cell. In various examples the cell or cell culture includes a cell or cells of *N. gaditana, N. oceanica*, or *N. salina*.

Optionally, the SL-homologous sequence used to identify or isolate at least one nucleic acid molecule can be operably liked to or juxtaposed with a heterologous sequence, e.g., a random sequence, a sequence that hybridizes with another nucleic acid molecule, or a sequence that facilitates amplification or cloning, for example, a restriction endonuclease recognition sequence, a sequence recognized by a recombinase or topoisomerase, or a sequence with homology to a primer, vector, or genomic sequence for recombinational cloning or homologous recombination into a host genome. The SL-homologous sequence can optionally comprise or be directly or indirectly bound to a detectable label or small molecule, such as a hapten, that for detection can in turn can be recognized (bound) by a protein and/or directly or indirectly by at least one antibody where the protein or at least one antibody can be labeled or can be linked or bound to a moiety that is labeled or that generates a detectable signal. Additionally or alternatively, the SL-homologous sequence can be covalently or noncovalently bound to a solid support, such as, but not limited to, a bead, column matrix, filter, or solid surface. The nucleic acid molecule can in some examples be a nucleic acid molecule as disclosed herein having a length of less than 250 nucleotides, and can be an oligonucleotide, i.e., a nucleic acid molecule having a length of less than or equal to 100 nucleotides. The nucleic acid molecule can include a nucleic acid sequence having at least 80%, for example at least 83%, at least 85%, at least 86%, at least 87%, at least 88%, such as about 89%, at least 90%, at least 91%, at least 92%, at least 93%, at least 94%, at least 95%, or 100% sequence identity to a nucleic acid sequence selected from the group consisting of SEQ ID NO:1, SEQ ID NO:2, SEQ ID NO:3, SEQ ID NO:4, SEQ ID NO:5, SEQ ID NO:6, and a complement of any thereof. For example, the nucleic acid molecule can comprise a nucleic acid sequence having at least 80%, for example at least 83%, at least 85%, at least 86%, at least 87%, at least 88%, such as about 89%, at least 90%, at least 91%, at least 92%, at least 93%, at least 94%, at least 95%, or 100% sequence identity to a nucleic acid sequence selected from the group consisting of SEQ ID NO:2, SEQ ID NO:3, SEQ ID NO:4, and complements thereof. Alternatively or in addition, the nucleic acid molecule can comprise a nucleic acid according to SEQ ID NO:5 or SEQ ID NO:6, or complements thereof. In particular examples, the nucleic acid molecule can comprise a nucleic acid sequence having at least 95% identity to a nucleic acid sequence selected from the group consisting of SEQ ID NO:2, SEQ ID NO:3, SEQ ID NO:4, and complements thereof. In some examples, the nucleic acid molecule can comprise a nucleic acid sequence selected from the group consisting of SEQ ID NO:2, SEQ ID NO:3, SEQ ID NO:4, and complements thereof.

Accordingly, in some examples, there is provided a method for identifying and/or isolating messenger RNA molecules from a population of RNA molecules. The method includes: providing a population of RNA molecules, adding to the population of RNA molecules one or more oligonucleotides or nucleic acid molecules of the present invention, for example, one or more nucleic acid molecules or oligonucleotides complementary to a nucleic acid sequence having at least 80%, 83%, 85%, 86%, 87%, 88%, such as about 89% or at least 90%, 91%, 92%, 93%, 94%, 95%, or 100% sequence identity to a nucleic acid sequence selected from the group consisting of SEQ ID NO:1, SEQ ID NO:2, SEQ ID NO:3, SEQ ID NO:4, SEQ ID NO:5, SEQ ID NO:6; allowing the one or more oligonucleotides or nucleic acid molecules of the present invention to bind or hybridize to one or more messenger RNA molecules of the population of RNA molecules, and optionally separating the messenger RNA molecules of the population of RNA molecules that are bound to the one or more oligonucleotides or nucleic acid molecules of the present invention from the unbound RNA molecules of the population of RNA molecules. Separation can be by any feasible means, for example, the nucleic acid molecule of the invention may be bound to a solid support, such as a column, bead, or membrane, for capture of trans-spliced RNAs, and nucleic acid molecules that do not hybridize to the nucleic acid molecule or oligonucleotide may be removed by washing.

The population of RNA molecules according to this aspect of the invention can be partially purified or substantially purified from a cell, one or more organisms, or cultures. Purification procedures for RNA are well known in the art, and can include, for example, lysis of cells, pulverization, homogenization, or maceration of tissue, denaturation of proteins, centrifugation, precipitation, extraction with organic solvents, enzymatic digestion, etc. In certain embodiments of the invention, the RNA population is provided in a crude lysate of cells or tissue that can optionally be treated, for example, with RNAse-free DNAse to remove DNA from the population.

In some examples, the present invention provides a method for identifying and/or isolating cDNA molecules from a population of cDNA molecules. The method includes: providing a population of cDNA molecules, adding to the population of cDNA molecules one or more oligonucleotides or nucleic acid molecules as provided herein that includes a spliced leader or spliced leader-homologous sequence, allowing the one or more oligonucleotides or nucleic acid molecules of the present invention to bind or hybridize to one or more cDNA molecules of the population of cDNA molecules, and optionally separating the cDNA molecules of the population of cDNA molecules that are bound to the one or more oligonucleotides or nucleic acid molecules of the present invention from the unbound cDNA molecules of the population of cDNA molecules. The population of cDNA molecules can include single-stranded cDNAs or double-stranded cDNAs. Providing a population of cDNA molecules can be by reverse transcription of a population of RNA molecules. As described in further detail at Example 3 below, oligonucleotide primers that include a SL sequence of the invention are very useful in cDNA synthesis, where their use in cDNA synthesis results in isolation of a high percentage of full-length cDNAs.

Methods for identifying an RNA or cDNA can optionally include sequencing at least one cDNA, e.g. a cDNA synthesized from the RNA template. Alternatively or in addition, identifying can further include hybridization of the RNA or cDNA with a specific probe.

The method described herein can be used with small amounts of total RNA as starting material and can be applied to a variety of samples and thus has several potential applications. For example, as the spliced leader has been determined to be present only on mRNA transcribed from nuclear genes, this method permits the isolation of mRNAs and the selective synthesis, amplification and/or cloning of cDNAs produced from these mRNAs that are tagged with an SL.

The mRNA and resulting cDNA can be present in mixtures including large amounts of non-trans-spliced mRNAs. For example, use of an oligonucleotide that includes a spliced leader sequence such as a spliced leader sequence provided herein, e.g., can allow for isolation and identification or cloning of transcripts of a heterokont species present in a mixed culture that includes one or more other species (that may, for example, be contaminants in a culture system). For example, the method described herein can also be used for the characterization of the trans-spliced transcriptome from organisms in mixed pools, for example, of the transcriptome of a *Nannochloropsis* species from a culture or environment (e.g., an outdoor growth environment such as a pond or raceway) that may also include non-*Nannochloropsis* species.

Thus, in some examples, oligonucleotide primers of the present invention can be used to collect and isolate nucleic acid molecules from a mixed culture. For example, such primers can be used as oligonucleotide probes on nucleic acid arrays in order to enrich for heterokont transcripts, or as oligonucleotide probes in colony hybridization experiments to isolate recombinant nucleic acid clones containing cDNAs having a 5' SL sequence tag. Methods and techniques for colony hybridization and array hybridization are well known in the art. Identified clones can be used for DNA isolation and sequencing to identify the cloned genes.

In additional examples, a population of mRNA molecules derived from a cell or a cell culture can be reverse transcribed using oligo-dT, random primers, degenerate primers, or specific primers to generate first cDNA strands and the resulting first strand cDNAs can be converted to double-stranded cDNAs using an oligonucleotide that includes a SL-homologous sequence as provided herein. Thus, the present invention provides a method for synthesizing cDNA comprising: hybridizing a 3' primer to a population of RNA molecules, in which a 3' primer is any primer that can hybridize to an RNA molecule and prime synthesis of cDNA in a 5' to 3' direction using the mRNA as a template (e.g., a primer comprising oligodT, a gene-specific or gene-family specific primer, a population of random primers, a degenerate primer, etc.); reverse transcribing a first strand of cDNA using at least one polymersase (e.g., a reverse transcriptase); hybridizing an nucleic acid molecule of the invention to the first strand of cDNA; and synthesizing a second strand of cDNA using at least one polymerase to produce a double-stranded DNA. The methods can be used to produce cDNA libraries, where the libraries are enriched for full-length cDNAs, and can be used to produce species-specific cDNA populations or libraries from mixed-species samples, for example, outdoor pond samples.

Synthesized cDNA molecules can be cloned, for example, in *E. coli*, and thereby amplified in the host strain for isolation of DNA and sequencing, or particular nucleic acids can alternatively or in addition be amplified, for example, by PCR, and cloned or directly sequenced. Methods of synthesizing cDNA from mRNA are well-known in the art and described in various methods books and publications as referenced herein. Enzymes and kits are also available commercially for cDNA synthesis.

For example, one or more cDNAs synthesized using a SL oligonucleotide as a 5' primer can optionally be amplified, e.g. by PCR, where the amplification can optionally also use a 5' PCR primer comprising an SL homologous sequence as disclosed herein. The 3' primer used in amplification can be the same 3' primer used for cDNA synthesis, or can be any other primer, for example, a gene-specific or gene-family specific primer, a random primer, a degenerate primer, etc.

Thus, in particular examples, the identifying or isolating method disclosed herein further comprises amplifying a nucleic acid sequence of the population of nucleic acid molecules by using at least one primer comprising a nucleic acid molecule of the invention that includes a spliced leader or spliced leader-homologous sequence as disclosed herein. In a particularly preferred embodiment, the amplification is performed by polymerase chain reaction (PCR) and the PCR template comprises reverse transcription products (cDNAs) derived from an RNA sample isolated from a cell or cell culture.

In one embodiment, PCR is performed with a first primer selected from the group consisting of: a nucleic acid sequence having at least 80%, at least 85%, at least 87%, at least 88%, about 89%, at least 90%, at least 91%; at least 92%, at least 93%, at least 94%, at least 95%, at least 96%, at least 97%, at least 98%, at least 99%, or 100% sequence identity to a nucleic acid sequence selected from the group consisting of SEQ ID NO:1, SEQ ID NO:2, SEQ ID NO:3, SEQ ID NO:4, SEQ ID NO:5, SEQ ID NO:6, and a complement of any thereof; and optionally with oligo-dT, one or more gene-specific primers, a population or degenerate primers, or a population of random primers as the second primer. In some preferred embodiment, the cell can be a heterokont cell. In some particularly preferred embodiments, the heterokont can be a species of *Nannochloropsis*.

Additionally, SL sequences can be used in conjunction with oligo-dT priming (or priming using a primer having a sequence occurring internal to the gene) of mRNA in reverse transcription/amplification to retrieve full-length sequences and the full complement of splice variants that may exist for a given heterokont gene. Further additionally, the SL sequences provided herein can be used as primers in amplification reactions following reverse transcription for enriching for *Nannochloropsis* transcripts in a mixed population such as in pond (especially when a reference dataset might not exist for a given species or strain), because, without being bound by theory, the SL sequence may specifically prime transcripts originating from a *Nannochloropsis* species or related species.

Oligonucleotide primers or probes of the present invention can optionally comprise or be conjugated to one or more detectable labels, specific binding members, polymers, peptides, polypeptides, nucleic acids, carbohydrates, lipids, steroids, enzymes, small molecules, protecting groups, or coupling agents. Coupling of oligonucleotide probes and primers to various organic molecules can be achieved by those skilled in the art of bioorganic synthesis. Methods of coupling oligonucleotide primers and probes to amino acids, peptides, and polypeptides can be through synthesis of a peptide (amide) bond as disclosed for the synthesis of peptide nucleic acids in, for example, Efimov, et al. *Russian Journal of Bioorganic Chemistry* 25: 545-555 (1999), or by using a linker, for example, as disclosed in U.S. Pat. No. 6,165, incorporated herein by reference. The coupling of oligonucleotide primers and probes of the present invention to additional nucleic acid molecules can also optionally be achieved through the use of a linker that can be added to an oligonucleotide probe or primer coupled to a solid support (Efimov 1999, supra; Finn et al., *Nucleic Acids Res.* 24: 3357-3364, 1996). Oligonucleotide probes and primers of the present invention can also be coupled to linkers that are in turn coupled to detectable labels, specific binding members, polymers, small molecules, matrices, polymers, and the like.

For detection of nucleic acids, one or more oligonucleotide primers or probes of the present invention can be provided on a solid support, which can be used repeatedly without degradation of the immobilized probes. Typically, an oligonucleotide primer or probe of the present invention that is attached to a solid support is from about six to about 1,000 residues in length, more typically from about 12 to about 60 residues in length.

In some examples, oligonucleotide primers or probes of the present invention can be covalently or noncovalently, reversibly or irreversibly, bound to a solid support. Reversible binding of an oligonucleotide primer or probe of the present invention to a solid support can be achieved through specific binding members or other means, for example, by electrostatic interactions (see, for example, PCT Patent Pub. No. WO200034521A1, herein incorporated by reference in its entirety). A solid support can comprise a membrane, such as a nitrocellulose or nylon membrane; paper (filter paper, cellulose). A solid support can also be a particle or bead that can comprise glass, can comprise one or more plastics or polymers, such as, for example, polystyrene, polyacrylamide, sepharose, agarose, cellulose or dextran, and/or can comprise metals, particularly paramagnetic metals, such as iron. A preferred solid support is a chip or array comprised of any suitable material (for example, a nylon membrane, a glass slide, an acrylamide layer, a plastic multiwell plate, etc.) to which a plurality of oligonucleotide primers or probes are directly or indirectly coupled. A number of different array configurations for nucleic acids, peptides, and peptide nucleic acids and methods for their production are known to those of skill in the art. Information in this regards can be found in, for example, U.S. Pat. Nos. 5,242,974; 5,384,261; 5,405,783; 5,412,087; 5,429,807; 5,436,327; 5,445,934; 5,472,672; 5,527,681; 5,545,531; 5,554,501; 5,571,639; 5,624,711; 5,658,734; 5,700,637; and 6,280,946; WO 99/60156, WO 01/38565, WO 99/60156, and WO 01/01144; the disclosures of which are herein incorporated by reference in their entireties. The processes of attachment and, where applicable, synthesis, of polymers on a solid support can be modified to those compatible with oligonucleotide primers and probes of the present invention.

Methods of hybridization, reverse transcription, second strand cDNA synthesis, and DNA amplification, e.g., polymerase chain reaction (PCR), and other molecular biology techniques are well-known in the art, and can be found in many molecular biology methods books, manuals from commercial suppliers of enzymes and reagents, and journal articles. For example, molecular biology manuals such as *Molecular Cloning: A Laboratory Manual* (4$^{th}$ ed., 2012) Green and Sambrook, Cold Spring Harbor Laboratory Press, Cold Spring Harbor, N.Y.; *PCR Protocols* Bartlett and Stirling (2$^{nd}$ ed. 2003) Human Press; and *Current Protocols in Molecular Biology* (Wiley Press, available online, www-.currentprotocolsonline); and others provide instruction on PCR techniques, RNA isolation, reverse transcription, cDNA synthesis, hybridization, labeling techniques, and the like.

Oligonucleotide Probes in Solution

In some examples, an oligonucleotide primer of the present invention used as a probe for the detection of target sequences in a sample can be provided in solution. An oligonucleotide primer of the present invention used as a probe for the detection of target sequences that is provided in solution can comprise a specific binding member, but that is not a requirement of the present invention. Preferred specific binding members are biotin, binding domains of proteins (for example, a calmodulin binding domain or a chitin binding domain), and a plurality of histidine residues, such that an oligonucleotide analogue probe can be captured by high affinity binding, for example, on an avidin, calmodulin, chitin, or nickel-NTA-coated surface of a solid support.

In embodiments where an oligonucleotide primer of the present invention that is provided in solution comprises a specific binding member and is used to capture complementary or substantially complementary nucleic acid molecules of the present invention, the nucleic acid molecules of the survey population are optionally labeled.

In some preferred embodiments of the present invention, after hybridizing oligonucleotide primer and nucleic acid molecules in solution, and subsequently capturing oligonucleotide primer moieties to a solid support, such as through the use of specific binding members, the hybridized oligonucleotide primer/nucleic acid molecule complexes can be detected by staining with intercalating dyes, such as but not limited to, ethidium bromide, ethidium homodimers, cyanine monomeric and cynanine dimeric stains. Such intercalating dyes will not stain oligonucleotide primer, but will stain nucleic acid molecules hybridized to oligonucleotide primers with high sensitivity, providing a simple and reliable way of detecting hybridized nucleic acid molecules.

It is also possible to hybridize oligonucleotide primers and nucleic acid molecules in solution, and electrophorese the hybridized complexes on a gel or matrix (for example an acrylamide or agarose gel). The gel or matrix can then be stained with an intercalating dye such as, for example, ethidium homodimer. It is also possible to stain the hybridized complexes in solution, prior to electrophoresis, with dyes such as ethidium homodimer, whose binding is stable to electrophoresis.

In an alternative method, an oligonucleotide primer of the present invention that is provided in solution to be used as a probe for the detection of target sequences optionally comprises a specific binding member. An oligonucleotide probe comprising a specific binding member can be hybridized to unlabeled target nucleic acid molecules, the target nucleic acid molecule/oligonucleotide probe complexes can be captured on a solid support comprising a complementary specific binding member, and subsequently the bound target nucleic acid molecules can be detected by hybridization of a labeled signal oligonucleotide, or signal oligonucleotide primer, or by binding of a specific binding member such as an antibody that can recognize nucleic acid molecule/oligonucleotide primer complexes.

In yet other embodiments, target nucleic acid molecules can be captured to a solid support using an oligonucleotide probe that comprises a specific binding member, and polymerase reactions can be performed using captured target nucleic acid molecules as templates. Such polymerase reactions may or may not incorporate a detectable label into their products. (For example, non-labeled amplification products may be electrophoresed on gels, and subsequently detected by staining, or may be sequenced, etc.). Such polymerase reactions can be done on a solid support or following release from a solid support, and can use one or more primers that are provided after the capture of the target nucleic acid molecules.

In certain aspects, the present invention includes kits for use in identification and/or isolation of a nucleic acid molecule from a cell or cell culture that include at least one oligonucleotide primer of the present invention and one or more of the following: a solid support such as beads, typically comprising at least one specific binding member, an oligodT-containing oligonucleotide, a population of random primers, one or more buffers or solutions, water, such as DEPC-treated or HPLC grade water, one or more useful enzymes (e.g. RNA polymerase, DNA polymerase, DNAses, RNAses), one or more precipitation reagents, one or more useful buffers, plastic ware (such as tubes or plates), and one or more filters. The oligonucleotide SL primer and/or the oligo dT primer can be provided linked to a specific binding member.

The discussion of the general methods given herein is intended for illustrative purposes. Other alternative methods and embodiments will be apparent to those of skill in the art upon review of this disclosure, and are to be included within the spirit and purview of this application. Additionally or alternatively to any of the above description, the present invention can include one or more of the following embodiments:

Embodiment 1

An isolated nucleic acid molecule comprising a nucleic acid sequence having at least 80% sequence identity to a nucleic acid sequence selected from the group consisting of SEQ ID NO:1, SEQ ID NO:2, SEQ ID NO:3, SEQ ID NO:4, SEQ ID NO:5, SEQ ID NO:6, and a complement of any thereof; wherein said nucleic acid molecule is less than or equal to 250 nucleotides, less than or equal to 200 nucleotides, less than or equal to 180 nucleotides, less than or equal to 150 nucleotides, less than or equal to 120 nucleotides, less than or equal to 100 nucleotides, less than or equal to 80 nucleotides, or less than or equal to about 65 nucleotides in length; wherein the isolated or recombinant nucleic acid molecule is double-stranded or at least partially single-stranded, optionally wherein the isolated nucleic acid molecule is a DNA molecule, and optionally wherein the isolated or recombinant nucleic acid molecule comprises a detectable label or binding moiety and/or is bound to a solid support.

Embodiment 2

An isolated nucleic acid molecule comprising an SL-homologous nucleic acid sequence having at least 80%, at least 83%, at least 85%, at least 86%, at least 87%, at least 88%, about 89%, at least 89%, at least 90%, at least 94%, at least 95%, or 100% sequence identity to a nucleic acid sequence selected from the group consisting of SEQ ID NO:1, SEQ ID NO:2, SEQ ID NO:3, SEQ ID NO:4, SEQ ID NO:5, SEQ ID NO:6, and a complement of any thereof; wherein the SL-homologous nucleic acid sequence is operably linked to at least one heterologous nucleic acid sequence, wherein at least one heterologous nucleic acid sequence is a regulatory sequence or a protein-encoding sequence.

Embodiment 3

An isolated or recombinant nucleic acid molecule according to Embodiment 2, wherein the heterologous nucleic acid sequence is a promoter, further wherein the promoter is derived from the same species as the SL-homologous nucleic acid sequence, further wherein the species is a heterokont, Eustigmatophyte, or *Nannochloropsis* species, optionally wherein the isolated or recombinant nucleic acid molecule is a vector.

Embodiment 4

An isolated or recombinant nucleic acid molecule according to Embodiment 2, wherein the heterologous nucleic acid sequence is a protein-encoding sequence, further wherein the protein-encoding sequence is not 100% identical to a protein-encoding sequence of the same species from which the SL-homologous sequence is derived, or is derived from a different species from the SL-homologous nucleic acid sequence, for example, is not a protein-encoding sequence of *Nannochloropsis gaditana, Nannochloropsis oceanica*, or *Nannochloropsis salina*, optionally wherein the isolated or recombinant nucleic acid molecule is a vector.

Embodiment 5

A recombinant host cell comprising a nucleic acid molecule according to any of claims 2-4, wherein any of the following are fulfilled: the host cell is a microorganism; the host cell is an algal or heterokont; the host cell is a diatom; the host cell is a Eustigmatophyte; the host cell is a species of *Eustigmatos, Monodus, Nannochloropsis*, or *Vischeria*; the host cell is a *Nannochloropsis* species; the host cell is *N. gaditana, N. oceanica*, or *N. salina*.

Embodiment 6

A method for identifying or isolating a nucleic acid molecule from a cell, optionally in a mixed cell culture, comprising (1) hybridizing at least one primer comprising a nucleic acid molecule according to embodiment 1 with a population of nucleic acid molecules derived from said cell, optionally further including one or more of the following steps:
(2) performing a reverse transcription reaction to produce a first strand of cDNA using a 3' primer for first strand synthesis prior to said hybridizing (1), where the 3' primer for first strand synthesis is optionally a population of random primers, a degenerate primer, one or more gene-specific primers or gene family-specific primers, or a primer comprising oligo-dT;
(3) performing second strand cDNA synthesis following said hybridizing (1);
(4) amplifying said cDNA produced by step 2 and/or step 3, wherein amplifying is preferably by PCR using a 3' primer and a 5' primer comprising a nucleic acid sequence according to embodiment 1.

Embodiment 7

A method for enhancing expression of a gene of interest in a host cell, said method comprising expressing in said host cell a nucleic acid molecule according to embodiment 2 or 4, wherein said heterologous nucleic acid comprises a coding sequence for said gene of interest, optionally wherein said cell is any of the following: a heterokont, a diatom, a chytrid, a Eustigmatophyte, a *Nannochloropsis* species, a species selected from the group consisting of *N. gaditana, N. granulata, N. limnetica, N. maritime, N. oceanica, N. oculata*, and *N. salina*.

Embodiment 8

A kit for identifying or isolating a nucleic acid molecule from a cell or cell culture, and/or producing at least one cDNA molecule, said kit comprising at least a primer comprising a nucleic acid molecule according to embodiment 1 and one or more of the following: a solid support such as beads, optionally comprising at least one specific binding member; an oligo dT-containing oligonucleotide; a population of random primers; one or more buffers or solutions; water, such as DEPC-treated or HPLC grade water; one or more useful enzymes (e.g. one or more reverse transcriptases, one or more DNA polymerases, one or more DNAses, one or more RNAses); one or more precipitation reagents; plasticware (such as tubes or plates); and one or more filters; and optionally further comprising instructions for use.

Embodiment 9

An isolated or recombinant nucleic acid molecule comprising a nucleic acid sequence having at least 94% identity to a nucleic acid sequence selected from the group consisting of SEQ ID NO:2, SEQ ID NO:3, and SEQ ID NO:4, wherein the nucleic acid molecule is less than 250 nucleotides in length.

Embodiment 10

An isolated or recombinant nucleic acid molecule comprising a nucleic acid sequence according to SEQ ID NO:5 or SEQ ID NO:6, wherein the nucleic acid molecule is less than 250 nucleotides in length.

Embodiment 11

An isolated or recombinant nucleic acid molecule according to embodiment 9 or embodiment 10, wherein at least one of the following conditions is met:
(5) The nucleic acid molecule is less than 200 nucleotides in length
(6) The nucleic acid molecule is less than 180 nucleotides in length
(7) The nucleic acid molecule is less than 150 nucleotides in length
(8) The nucleic acid molecule is less than 120 nucleotides in length
(9) The nucleic acid molecule is less than 100 nucleotides in length
(10) The nucleic acid molecule is less than 80 nucleotides in length
(11) The nucleic acid molecule comprises or is bound to a detectable label or binding moiety
(12) The nucleic acid molecule is bound to a solid support
(13) The nucleic acid molecule is a DNA molecule
(14) The nucleic acid molecule is at least partially single-stranded Embodiment 12

An isolated or recombinant nucleic acid molecule according to any of embodiments 9-11, comprising a nucleic acid sequence selected from the group consisting of SEQ ID NO:2, SEQ ID NO:3, and SEQ ID NO:4.

Embodiment 13

A method for identifying or isolating a nucleic acid molecule, comprising, hybridizing the nucleic acid molecule of any of embodiments 9-12 to a population of RNA or cDNA molecules.

Embodiment 14

A method according to embodiment 13, further comprising synthesizing cDNA using at least one polymerase.

Embodiment 15

A method according to embodiment 14, further comprising amplifying said cDNA using a primer comprising a nucleic acid molecule according to any of embodiments 9-12.

It should also be understood that the following examples are offered to illustrate, but not limit, the invention.

EXAMPLES

The following examples are included merely for purposes of illustration of certain aspects and embodiments of the present invention, and are not intended to limit the invention in any way.

Example 1

Identification of Spliced Leader Sequences in Mature Transcripts from *Nannochloropsis* Species The SL sequences of the present invention were identified in numerous transcripts from the recently published *N. gaditana* CCMP526 genome (Radakovits et al. *Nat. Commun.* 3:686 doi: 10.1038/ncomms1688, 2012); see also, Whole Genome Shotgun Project (HGSP) website, available at Nannochloropsis.genomeprojectsolutions-databases.com). There are 37056 cDNA contigs in the "transcriptome_assembly.fa" file from the HGSP website. Specifically, we found that 2364 out of 37056 *N. gaditana* cDNA contigs in the "transcriptome_assembly.fa" file have an identical truncated version of the *N. gaditana* SL (SEQ ID NO:1) located upstream of the initiating AUG codon and within 50 bp of the cDNAs' 5' end. Of that subset, 133 have a longer, 18 bp motif (cctaagggaaaacaacag; SEQ ID NO:2). These motifs were not identified in the published sequences.

The full-length SL donor sequence (SEQ ID NO:7) was mapped to a putative donor site identified in a *Nannochloropsis gaditana* nuclear genome assembly (FIG. 1). A genome locus was also identified in the *N. salina* CCMP1776 genome (Qingdao Institute of BioEnergy and Bioprocess Technology, Chinese Academy of Sciences, i.e. CAS-QIBEBT) that matches the putative donor RNA of the *N. gaditana* genome, although this locus had not been identified in the *N. salina* CCMP1776 draft genome. Alignment of the *N. gaditana* SL donor template sequence (SEQ ID NO:7) to a portion of the *N. salina* CCMP1776 genome sequence (SEQ ID NO:8) is shown in FIG. 3. The sequence identity of the *N. salina* genome sequence with the *N. gaditana* SL donor locus strongly suggests that *N. salina* also uses trans-splicing to add leader sequences to mRNAs, and that at least one *N. salina* SL sequence (shown in bold within the box in FIG. 3) is identical to a SL sequence of *N. gaditana* (SEQ ID NO:2).

Figure 2:
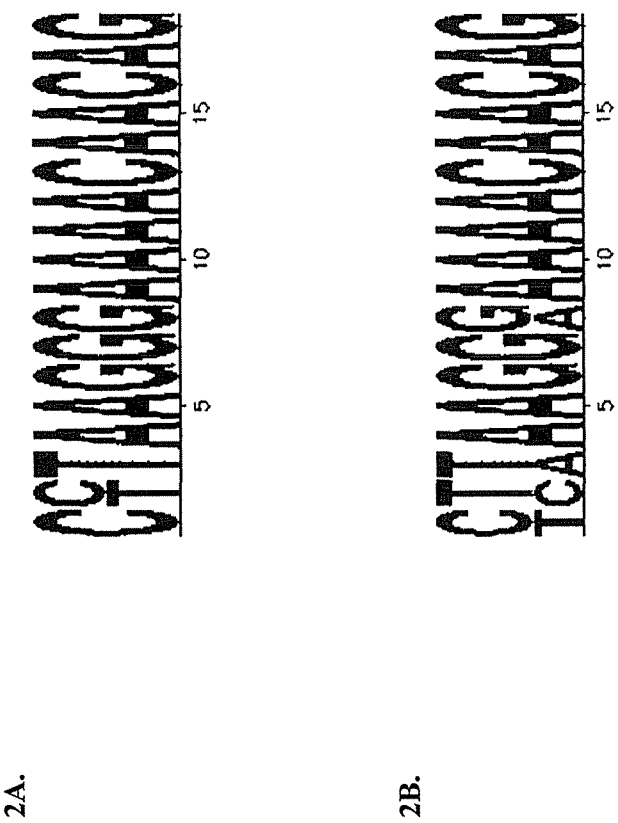
FIG. 2A and FIG. 2B is a graphical representation of a *Nannochloropsis gaditana* SL consensus motif (SEQ ID NO:5); a single nucleotide polymorphism in the 2 position is shown to indicate that cytosine is the major variant and thymidine the minor variant in this position.

Further analysis of an internal *N. gaditana* transcriptomics database revealed two variants of *N. gaditana* SL sequences, with a single nucleotide polymorphism in the 2 position; C was the major variant detected in 5653 transcripts, whereas the T-variant spliced leader (ctaagggaaaacaacag; SEQ ID NO:3) was found in 267 transcripts (FIG. 2A). None of the 133 *N. gaditana* sequences originally identified as comprising a spliced leader had the minor variant with T in the 2 position. The *Nannochloropsis* SL consensus motif is predicted to be approximately 18-23 nucleotides in length, for example, 18 nucleotides in length, with the consensus sequence "cytaagggaaaacaacag" (where "y" represents a pyrimidine) (SEQ ID NO:5).

In addition, a spliced leader sequence was identified in *Nannochloropsis oceanica*. The 18 nt version of this SL sequence was found as ttanaggaaaaacaacag (SEQ ID NO:4) at the 5' end of several transcripts in the strand-specific cDNA assembly for *N. oceanica* isolate WE5473. Based on these sequences, the heterokont SL consensus motif is predicted to be approximately 18-23 nucleotides in length, for example, 18 nucleotides in length, with the consensus sequence "yywaaggraaaacaacag" (SEQ ID NO:6) (FIG. 2B), where "Y" represents a pyrimidine; "R" represents a purine; and "W" represents an A or T (see, e.g. WIPO Standard ST.25, 1998, Appendix 2).

It is therefore expected that the SL sequence is conserved across all *N. gaditana*, *N. salina*, and *N. oceanica* strains, and it is likely that SL sequences homologous to the SL sequences discovered in these species exist in all *Nannochloropsis* species. SL sequences may occur in Eustigmatophytes in general (e.g., *Nannochloropsis*, *Eustigmatos*, *Monodus*, and *Vischeria* species) and possibly occur across the stramenopile lineage as well.

Example 2

Identification of SL Donor RNA Loci in *Nannochloropsis* Genomes

Applicants have subsequently identified several donor loci that encode the SL RNA that contributes the spliced leader. In fact, the major variant of the 18-nt SL sequence identified as described in Example 1 was found at 4 distinct loci located on chromosomes 7, 9, 24 and 27 in the *Nannochloropsis gaditana* genome. At each of these loci, the conserved 18-nt SL sequence was followed by a putative "GT" donor splice site. The nucleotide residues corresponding to the conserved SL sequence at each of the identified loci are listed below.

1) Ng_3730_7:230045 (SEQ ID NO:9)
2) Ng_3730_9:189744 (SEQ ID NO:10)
3) Ng_3730_24:546744 (SEQ ID NO:11)
4) Ng_373027:43 (SEQ ID NO:12)

An additional match was identified at Ng_3730_15: 391864, but the spliced leader sequence was followed by a GA not a GT and the extended sequence did not align as well with the other 4 SL donor sequence regions. In addition, a donor SL sequence region was also found for the minor variant at locus 5) Ng_3730_4:536775 (SEQ ID NO:13). The minor variant was also found to align well with the other 4 donor SL sequence regions over an extended region.

FIG. 4 provides a sequence alignment of the donor sequences from the 5 different genetic loci described above. The 5 putative donor sequences aligned perfectly (except for the minor variant substitution) over a stretch of 74 nucleotides, i.e. in addition to the 18 nt-SL conserved sequence, 42 nucleotides of sequence upstream and 14 nucleotides of sequence downstream aligned perfectly across donor loci.

Example 3

Identification and Selective Cloning of cDNA Molecules Tagged with a *Nannochloropsis* SL Sequence As discussed above, *Nannochloropsis* species use trans-splicing process to incorporate a taxon-specific sequence tag, i.e. the spliced leader, into either all or a significant fraction of their mRNAs. Applicants have exploited this feature to develop a method for the preparation of full-length enriched cDNA populations. The method involves PCR-amplification of SL-tagged cDNA and subsequent cloning of PCR products.

To isolate total RNA, 10 mLs of an algal cell culture was spun down at 4000×g for 5 minutes and the supernatant was decanted. The pellet was resuspended in 1.8 mL Buffer A (5 mL TLE Grinding Buffer, 5 mL phenol, 1 mL 1-bromo-3-chloropropane and 20 µL mercaptoethanol, where TLE Grinding Buffer includes 9 mL of 1M Tris pH 8, 5 mL of 10% SDS, 0.6 mL of 7.5 M LiCl, and 0.45 M EDTA, in a final volume of 50 mL) and transferred to a 2 mL microcentrifuge tube containing approximately 0.5 mL of 200 µm zirconium beads. The tube was vortexed vigorously for 5 min at 4° C. and then centrifuged for 2 min at 11.8×g. The aqueous layer was then removed and pipetted into a new 2 mL tube, to which 1 mL 25:24:1 phenol extraction buffer (25 mL phenol pH 8 or 5.1; 24 mL 1-bromo-3-chloropropane, and 1 mL isoamyl alcohol) was added and the tube was shaken vigorously and centrifuged for 2 min at 11.8×g. After centrifugation, the aqueous layer was removed and pipetted into a new 2 mL centrifuge tube, to which 1 ml 1-bromo-3-chloropropane was added. The tube was shaken and again centrifuged for 2 min at 11.8×g. The aqueous layer was removed to a new tube and 0.356 volumes of 7.5 M LiCl was added. The tube was inverted 10-12 times and stored at −20° C. overnight. The next day, samples were allowed to come to room temperature without mixing and were centrifuged at 16,000×g for 30 minutes. The supernatant was removed and the pellet was washed with 1 mL of ice cold 80% ethanol. The tube was centrifuged for 30 min at 16,000×g and allowed to air dry after the supernatant had been removed. Finally, the RNA pellet was resuspended in 50 µl ultrapure water. The RNA quality was assessed by on-chip gel electrophoresis using an Agilent 2100 Bioanalyzer and RNA6000 LabChip according to manufacturer instructions.

mRNAs were reversed transcribed and PCR-amplified by using three primer combinations using the SMARTer™ PCR cDNA Synthesis kit (Clontech) according to manufacturer's instructions (manual published January 2012). The primer combinations in separate reactions were as follows:

1) "Oligo dT" lanes: a 3' oligo dT primer paired with a commercial generic 5' primer (5' SMART primer from the Clontech SMARTer® cDNA synthesis kit);
2) "Random" lanes: a random 3' primer paired with a commercial generic 5' primer (Clontech 5' SMART primer); and
3) "SL+oligo dT" lanes: an Oligo dT 3' primer paired with a 5' primer that included a SL sequence (SEQ ID NO:2).

Figure 5:
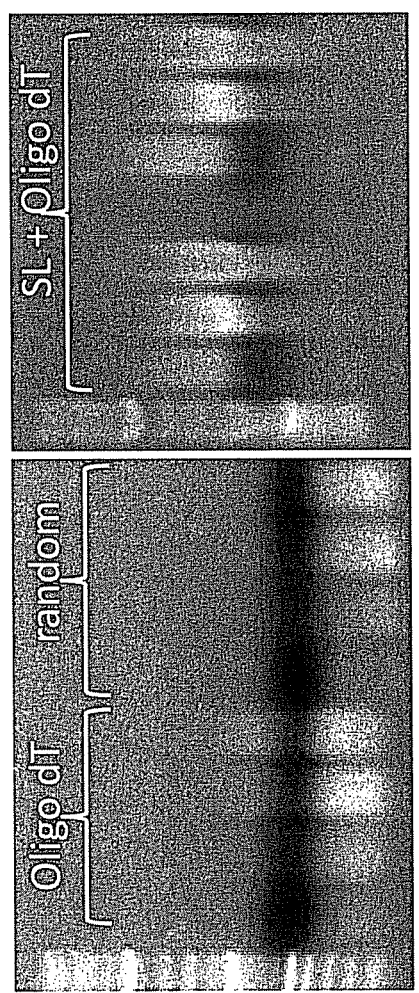

FIG. 5 depicts the results of an agarose gel electrophoresis analysis of cDNA products from *Nannochloropsis* sp. generated as described above. Gel photos show the quality of cDNA samples produced by using each of the three primer combinations. As judged by the higher molecular weight staining of the cDNA products, the SL primer paired with oligo dT resulted in much higher quality cDNA library, making the *Nannochloropsis* SL sequence disclosed herein extremely useful for producing cDNA libraries and isolating genes.

A total of 24 cDNA clones were subsequently isolated from a cDNA library synthesized from RNA using the spliced leader sequence as an upstream (5') primer as described above. These gene sequences were used to query sequences from public database sequences. When aligned with the closest known homolog, the SL-isolated clones were found to have complete or near complete coverage in nearly half of the cases. In fact, coverage was at least 80% in fourteen of the twenty-two clones. This finding indicates that primers that include the SL sequence can be very useful in cDNA synthesis where their use results in isolation of a high percentage of full-length cDNAs, and thus has several potential applications.

Construction of a Full-Length Enriched cDNA Library

Total RNA was isolated independently from four different growth conditions (e.g. nitrogen deprivation, phosphorous deprivation, and high light conditions) of *Nannochloropsis gaditana* by the extraction method described above. For isolation of mRNA, the FASTTRACK® MAG mRNA Isolation Kit for isolating high-quality mRNA from total RNA, cells, and tissue (Life Technologies, Carlsbad, Calif.) was used, following the manufacturer's recommended procedures. The mRNA quality was assessed by on-chip gel electrophoresis using an Agilent 2100 Bioanalyzer and RNA6000 LabChip according to manufacturer instructions. cDNA synthesis was performed with two primers each having a sequence extension that added nucleotide sequence compatible with a cloning vector to allow for subsequent IN-FUSION® cloning of the cDNA products into an expression vector (the 3'-most 18 nucleotides in lower case letters of SEQ ID NO:14, below, are spliced leader bases).

```
1) 5' primer containing SL sequence: MCA-1185
                                    (SEQ ID NO: 14)
5'-TTCCACCCAAGCAGTGGTATCAACGCAGAGTGGcctaagggaaaa
caacag-3'

2) 3' Oligo-dT-containing primer:
                                    (SEQ ID NO: 15)
5'-GTATCGATGCCCACCCTCTAGAGGCCGAGGCGGCCGACAcggtac
ccgcttttttttttt-3'
``` mRNA was reverse-transcribed with the oligo(dT)-containing primer (SEQ ID NO:15) as above, and the resultant cDNA was amplified by 15 cycles of PCRs with Pfu DNA polymerase using the SL-including primer (SEQ ID NO:14) and the oligo-(dT)-containing primer (SEQ ID NO:15). The amplified cDNAs were size-fractionated by gel chromatography. After treating with Taq DNA polymerase for 5 min at 72° C., the cDNA products were cloned into an expression vector using IN-FUSION® SMARTer™ Directional cDNA Library Construction Kit (Clontech Laboratories, Mountain View, Calif.) and transformed into *E. coli*. Approximately 750,000 *E. coli* colonies were collected and pooled to form a cDNA library. The insert sequences were determined by conventional procedures and then used to BLAST-searched against themselves and to query sequences from public sequence databases. Informatics analyses revealed that the cDNA library had no empty clones and little redundancy.

Our analyses of *Nannochloropsis gaditana* cDNAs revealed that approximately 65% (6282 of 9617 coding cDNAs examined) of nuclear gene cDNA transcripts had a SL. Because the SL primer has sequences in addition to the SL sequence itself, it is possible that some cDNAs resulted from internal priming. We hypothesize that most, and possibly all or nearly all, *Nannochloropsis gaditana* nuclear mRNAs include a spliced leader. No chloroplast-encoded transcripts were found to have a SL, which was consistent with reports from other organisms that trans-splicing of SL is restricted to nuclear RNAs (see, e.g. Zhang et al. *Proc. Natl. Acad. Sci. USA* 104:4618-4623, 2007). These gene sequences were used to query sequences from public database sequences and we found that these cDNAs encodes proteins of diverse functions along with numerous proteins of unknown function, indicating no preferred SL recipients.

Since the spliced leader has been determined to be present only on mRNA transcribed from nuclear genes, this method permits the selective synthesis, amplification and/or cloning of cDNAs produced from these nuclear mRNAs that are tagged with an SL.

A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives and equivalents are within the scope of the invention as described and claimed herein.

All publications and patent applications mentioned in this specification are herein incorporated by reference to the same extent as if each individual publication or patent application was specifically can individually indicated to be incorporated by reference. Throughout this disclosure, various information sources are referred to and are, where specifically noted, incorporated by reference. The information sources include, for example, World Wide Web browser-inactive page addresses. The reference to such information sources is solely for the purpose of providing an indication of the general state of the art at the time of filing. While the contents and teachings of each and every one of the information sources can be relied on and used by one of skill in the art to make and use embodiments of the invention, any discussion and comment in a specific information source should in no way be considered as an admission that such comment was widely accepted as the general opinion in the field.

Headings within the application are solely for the convenience of the reader, and do not limit in any way the scope of the invention or its embodiments.

What is claimed is:

1. A method of producing cDNA, comprising:
hybridizing at least one 3' primer to a population of RNA molecules isolated from a cell, wherein the at least one 3' primer is selected from the group consisting of: a population of random primers, a degenerate primer, one or more gene-specific primers, one or more gene family-specific primers, and a primer comprising oligo-dT, to generate a population of RNA molecules hybridized to the at least one 3' primer;
synthesizing a population of first strands of cDNA from the population of RNA molecules hybridized to the at least one 3' primer using at least one polymerase;
hybridizing a 5' primer comprising a nucleic acid sequence having at least 83% identity to a SL sequence selected from the group consisting of SEQ ID NO:2, SEQ ID NO:3, and SEQ ID NO:4 to the population of first strands of cDNA; and
synthesizing second strands of cDNA from the population of first strands of cDNA hybridized to the 5' primer to produce a population of double-stranded cDNA molecules.

2. The method of claim 1, further comprising amplifying at least one double-stranded cDNA molecule of the population of double-stranded cDNA molecules.

3. The method of claim 2, wherein the amplification is PCR and the PCR is performed using at least one primer selected from the group consisting of a gene-specific primer, a gene family-specific primer, a primer comprising oligo-dT, a population of random primers, and a population of degenerate primers.

4. The method of claim 2, wherein amplification is performed using a 5' primer comprising a nucleic acid sequence having at least 83% identity to a SL sequence selected from the group consisting of SEQ ID NO:2, SEQ ID NO:3, and SEQ ID NO:4.

5. The method of claim 4, wherein amplification is performed using a 5' primer comprising a nucleic acid sequence having at least 88% identity to an SL sequence selected from the group consisting of SEQ ID NO:2, SEQ ID NO:3, and SEQ ID NO:4.

6. The method of claim 5, wherein amplification is performed using a 5' primer comprising a nucleic acid sequence having at least 94% identity to an SL sequence selected from the group consisting of SEQ ID NO:2, SEQ ID NO:3, and SEQ ID NO:4.

7. The method of claim 6, wherein amplification is performed using a 5' primer comprising a nucleic acid sequence selected from the group consisting of SEQ ID NO:2, SEQ ID NO:3, and SEQ ID NO:4.

8. The method of claim 1, wherein the cell is a heterokont cell.

9. The method of claim 8, wherein the cell is a Eustigmatophyte cell.

10. The method of claim 9, wherein the cell is a *Nannochloropsis* cell.

11. The method of claim 1, wherein the 5' primer has a length of from 15 to 250 nucleotides.

12. The method of claim 11, wherein the 5' primer has a length of from 15 to 100 nucleotides.

13. The method of claim 1, further comprising cloning one or more of the double-stranded cDNA molecules in *E. coli*.

14. The method of claim 1, further comprising sequencing at least one double-stranded cDNA molecule.

15. The method of claim 1, wherein the 5' primer comprises a nucleic acid sequence having at least 88% identity to a SL sequence selected from the group consisting of SEQ ID NO:2, SEQ ID NO:3, and SEQ ID NO:4.

16. The method of claim 15, wherein the 5' primer comprises a nucleic acid sequence having at least 94% identity to a SL sequence selected from the group consisting of SEQ ID NO:2, SEQ ID NO:3, and SEQ ID NO:4.

17. The method of claim 16, wherein the 5' primer comprises a nucleic acid sequence selected from the group consisting of SEQ ID NO:2, SEQ ID NO:3, and SEQ ID NO:4.

* * * * *

SEQUENCE LISTING

```
<160> NUMBER OF SEQ ID NOS: 15

<210> SEQ ID NO 1
<211> LENGTH: 11
<212> TYPE: DNA
<213> ORGANISM: Nannochloropsis gaditana
<220> FEATURE:
<221> NAME/KEY: misc_feature
<223> OTHER INFORMATION: truncated spliced leader

<400> SEQUENCE: 1
gaaaacaaca g                                                        11
```

<210> SEQ ID NO 2
<211> LENGTH: 18
<212> TYPE: DNA
<213> ORGANISM: Nannochloropsis gaditana
<220> FEATURE:
<221> NAME/KEY: misc_feature
<223> OTHER INFORMATION: spliced leader, major variant

<400> SEQUENCE: 2
cctaagggaa aacaacag                                                 18

<210> SEQ ID NO 3
<211> LENGTH: 18
<212> TYPE: DNA
<213> ORGANISM: Artificial Sequence
<220> FEATURE:
<221> NAME/KEY: misc_feature
<223> OTHER INFORMATION: spliced leader, minor variant

<400> SEQUENCE: 3
cttaagggaa aacaacag                                                 18

<210> SEQ ID NO 4
<211> LENGTH: 18
<212> TYPE: DNA
<213> ORGANISM: Nannochloropsis oceanica
<220> FEATURE:
<221> NAME/KEY: misc_feature
<223> OTHER INFORMATION: spliced leader

<400> SEQUENCE: 4
ttaaaggaaa aacaacag                                                 18

<210> SEQ ID NO 5
<211> LENGTH: 18
<212> TYPE: DNA
<213> ORGANISM: Artificial Sequence
<220> FEATURE:
<221> NAME/KEY: misc_feature
<223> OTHER INFORMATION: Consensus Nannochloropsis gaditana spliced
      leader sequence

<400> SEQUENCE: 5
cytaagggaa aacaacag                                                 18

<210> SEQ ID NO 6
<211> LENGTH: 18
<212> TYPE: DNA
<213> ORGANISM: Artificial Sequence
<220> FEATURE:
<221> NAME/KEY: misc_feature
<223> OTHER INFORMATION: Consensus Nannochloropsis spliced leader
      sequence

<400> SEQUENCE: 6
yywaaggraa aacaacag                                                 18

<210> SEQ ID NO 7
<211> LENGTH: 54
<212> TYPE: DNA
<213> ORGANISM: Nannochloropsis gaditana
<220> FEATURE:
<221> NAME/KEY: misc_feature
<223> OTHER INFORMATION: spliced leader donor locus
<220> FEATURE:
<221> NAME/KEY: misc_feature
<222> LOCATION: (47)..(54)

<223> OTHER INFORMATION: Consensus Nannochloropsis spliced leader
       sequence

<400> SEQUENCE: 7
cagtaaagta ttcaagaata aacaaacaaa acaatcccta agggaaaaca acag        54

<210> SEQ ID NO 8
<211> LENGTH: 54
<212> TYPE: DNA
<213> ORGANISM: Nannochloropsis salina
<220> FEATURE:
<221> NAME/KEY: misc_feature
<223> OTHER INFORMATION: spliced leader donor locus
<220> FEATURE:
<221> NAME/KEY: misc_feature
<222> LOCATION: (47)..(54)
<223> OTHER INFORMATION: Consensus Nannochloropsis spliced leader
       sequence

<400> SEQUENCE: 8
cagtaaagta ttcaagaata aacaaacaaa acaatcccta agggaaaaca acag        54

<210> SEQ ID NO 9
<211> LENGTH: 218
<212> TYPE: DNA
<213> ORGANISM: Nannochloropsis gaditana
<220> FEATURE:
<221> NAME/KEY: misc_feature
<223> OTHER INFORMATION: spliced leader donor locus Ng_3730_7:230045
<220> FEATURE:
<221> NAME/KEY: misc_feature
<222> LOCATION: (101)..(118)
<223> OTHER INFORMATION: Consensus Nannochloropsis spliced leader
       sequence

<400> SEQUENCE: 9
tcacaccctg gttgtggccc atggggtata gagggaggag tgtttctcca cctcgctcaa      60
ttttcagtaa agtattcaag aataaacaaa caaacaatc cctaagggaa acaacaggt      120 aatttgagct tcccaagcac atcaccctcc agacaatcgc gttgaaaccc tcctagatcc     180
ctaaccaacc ttaccacacc atgccgtagg tcacatgc                            218

<210> SEQ ID NO 10
<211> LENGTH: 218
<212> TYPE: DNA
<213> ORGANISM: Nannochloropsis gaditana
<220> FEATURE:
<221> NAME/KEY: misc_feature
<223> OTHER INFORMATION: spliced leader donor locus Ng_3730_9:189744
<220> FEATURE:
<221> NAME/KEY: misc_feature
<222> LOCATION: (101)..(118)
<223> OTHER INFORMATION: Consensus Nannochloropsis spliced leader
       sequence

<400> SEQUENCE: 10
tcacactctg gttgtggccc atgggtacg tagggaggag tgtttctccg cctctcccaa      60
ttttcagtaa agtattcaag aataaacaaa caaacaatc cctaagggaa acaacaggt      120 aatttgagct ttccaagcac atcaccctcc ggataaccac gatgaacccc acctagatcc    180
ctaaacaatg attcttgatg ggaaggtatc ggcggttc                            218

<210> SEQ ID NO 11
<211> LENGTH: 218
<212> TYPE: DNA
<213> ORGANISM: Nannochloropsis gaditana
<220> FEATURE:

```
<221> NAME/KEY: misc_feature
<223> OTHER INFORMATION: spliced leader donor locus Ng_3730_24:546744
<220> FEATURE:
<221> NAME/KEY: misc_feature
<222> LOCATION: (101)..(118)
<223> OTHER INFORMATION: Consensus Nannochloropsis spliced leader
      sequence

<400> SEQUENCE: 11
tcacactctg gttgtggccc atcgggtccg tcgggaggag tgtttctccg tccatctcaa    60
ttttcagtaa agtattcaag ataaacaaa caaaacaatc cctaagggaa acaacaggt    120 aatttgagct tcccaagcgc atcaccctcc agacatccac actgaacccc acctagatcc   180
ctaaactacc ttcccacacg ccctcctggc tcatgcgt                           218

<210> SEQ ID NO 12
<211> LENGTH: 161
<212> TYPE: DNA
<213> ORGANISM: Nannochloropsis gaditana
<220> FEATURE:
<221> NAME/KEY: misc_feature
<223> OTHER INFORMATION: spliced leader donor locus Ng_3730_27:43
<220> FEATURE:
<221> NAME/KEY: misc_feature
<222> LOCATION: (44)..(61)
<223> OTHER INFORMATION: Consensus Nannochloropsis spliced leader
      sequence

<400> SEQUENCE: 12
caattttcag taaagtattc aagaataaac aaacaaaaca atccctaagg gaaaacaaca    60
ggtaatttga gctttccaag cgcactaccc tccagaccac cactatgaac cccacctaga   120
tccctaaaca acctcaacac gtacacgtct gcccataccc t                       161

<210> SEQ ID NO 13
<211> LENGTH: 218
<212> TYPE: DNA
<213> ORGANISM: Nannochloropsis gaditana
<220> FEATURE:
<221> NAME/KEY: misc_feature
<223> OTHER INFORMATION: spliced leader donor locus Ng_3730_4:536775
<220> FEATURE:
<221> NAME/KEY: misc_feature
<222> LOCATION: (101)..(118)
<223> OTHER INFORMATION: Consensus Nannochloropsis spliced leader
      sequence

<400> SEQUENCE: 13
tcacactctg gttgtggccc atcgtgtata tagggagcag tgtttcctct cttctcccaa    60
ttttcagtaa agtattcaag ataaacaaa caaaacaatc cttaagggaa acaacaggt    120 aatttgagct ttccaagcac actaccctcc agacacctac aacgaacccc acctagatcc   180
ctaaactacc tcacctcgtc tttccttcac atccacac                           218

<210> SEQ ID NO 14
<211> LENGTH: 51
<212> TYPE: DNA
<213> ORGANISM: Artificial Sequence
<220> FEATURE:
<221> NAME/KEY: misc_feature
<223> OTHER INFORMATION: PCR primer MCA-1185

<400> SEQUENCE: 14
ttccacccaa gcagtggtat caacgcagag tggcctaagg gaaaacaaca g             51

<210> SEQ ID NO 15
```

```
<211> LENGTH: 60
<212> TYPE: DNA
<213> ORGANISM: Artificial Sequence
<220> FEATURE:
<221> NAME/KEY: misc_feature
<223> OTHER INFORMATION: Oligo-dT PCR primer

<400> SEQUENCE: 15
gtatcgatgc ccaccctcta gaggccgagg cggccgacac ggtacccgct tttttttttt        60
```